(12) United States Patent
Goldfarb et al.

(10) Patent No.: US 8,846,747 B2
(45) Date of Patent: Sep. 30, 2014

(54) COMPOUNDS AND METHODS FOR ALTERING LIFESPAN OF EUKARYOTIC ORGANISMS

(75) Inventors: David S. Goldfarb, Victor, NY (US); Joseph A. Maddry, Birmingham, AL (US); Lynn Rasmussen, Odenville, AL (US); Ellie Lucille White, Birmingham, AL (US); Krister Wennerberg, Helsinki (NO)

(73) Assignees: University of Rochester, Rochester, NY (US); Southern Research Institute, Birmingham, AL (US)

( * ) Notice: Subject to any disclaimer, the term of this patent is extended or adjusted under 35 U.S.C. 154(b) by 50 days.

(21) Appl. No.: 13/510,166

(22) PCT Filed: Nov. 17, 2010

(86) PCT No.: PCT/US2010/056990
§ 371 (c)(1),
(2), (4) Date: Jan. 3, 2013

(87) PCT Pub. No.: WO2011/062964
PCT Pub. Date: May 26, 2011

(65) Prior Publication Data
US 2013/0096175 A1    Apr. 18, 2013

Related U.S. Application Data

(60) Provisional application No. 61/261,851, filed on Nov. 17, 2009.

(51) Int. Cl.
| | | |
|---|---|---|
| A61K 31/405 | (2006.01) |
| A61K 31/135 | (2006.01) |
| A61K 31/12 | (2006.01) |
| C07D 307/02 | (2006.01) |
| C07C 49/00 | (2006.01) |
| C07C 49/753 | (2006.01) |
| C07D 317/54 | (2006.01) |
| C07C 49/577 | (2006.01) |
| C07D 307/54 | (2006.01) |
| C07D 333/22 | (2006.01) |
| C07C 49/417 | (2006.01) |
| C07D 209/12 | (2006.01) |
| C07C 49/792 | (2006.01) |
| C07D 319/18 | (2006.01) |
| C07C 49/403 | (2006.01) |
| C07C 235/82 | (2006.01) |
| C07C 49/657 | (2006.01) |
| C07D 307/46 | (2006.01) |
| C07C 49/573 | (2006.01) |
| C07C 49/543 | (2006.01) |
| C07C 49/613 | (2006.01) |
| C07C 49/567 | (2006.01) |
| C07C 69/757 | (2006.01) |
| C07C 49/553 | (2006.01) |
| C07C 225/22 | (2006.01) |
| C07C 69/743 | (2006.01) |

(52) U.S. Cl.
CPC .......... *C07C 49/657* (2013.01); *C07C 2102/42* (2013.01); *C07C 49/753* (2013.01); *C07D 317/54* (2013.01); *C07C 49/577* (2013.01); *C07D 307/54* (2013.01); *C07D 333/22* (2013.01); *C07C 49/417* (2013.01); *C07D 209/12* (2013.01); *C07C 49/792* (2013.01); *C07D 319/18* (2013.01); *C07C 2101/08* (2013.01); *C07C 49/403* (2013.01); *C07C 235/82* (2013.01); *C07C 2101/02* (2013.01); *C07D 307/46* (2013.01); *C07C 49/573* (2013.01); *C07C 49/543* (2013.01); *C07C 2101/14* (2013.01); *C07C 49/613* (2013.01); *C07C 49/567* (2013.01); *C07C 69/757* (2013.01); *C07C 49/553* (2013.01); *C07C 225/22* (2013.01); *C07C 69/743* (2013.01)
USPC .......... 514/415; 514/647; 514/691; 514/684; 549/498; 568/367; 568/368; 568/683

(58) Field of Classification Search
CPC .. C07D 209/08; C07D 209/12; C07D 209/14; C07D 209/16; C07D 401/12; C07D 307/04; C07D 307/46; C07D 2/14
USPC ................. 514/415, 647, 691, 684; 549/498; 568/367, 368, 683
See application file for complete search history.

(56) References Cited

U.S. PATENT DOCUMENTS

| | | |
|---|---|---|
| 4,695,673 A | 9/1987 | Heather et al. |
| 4,760,192 A | 7/1988 | Warner et al. |

(Continued)

FOREIGN PATENT DOCUMENTS

| | | |
|---|---|---|
| DE | 32 19490 A1 | 12/1983 |
| EP | 0501822 A1 | 2/1992 |

OTHER PUBLICATIONS

Hoiby Prospects for the prevention and control of pseudomonal infection in children . . . (Paediatr Drugs. Nov.-Dec. 2000;2(6):451-63).*

(Continued)

*Primary Examiner* — Shirley V Gembeh
(74) *Attorney, Agent, or Firm* — David P. Halstead; Foley Hoag LLP

(57) ABSTRACT

Provided are compounds which generally have a triketone structure. Examples of the compounds include derivatives of 1,3-cyclohexanedione, such as: 1,3-cyclohexanedione, 2-propanoyl-5-cyclohexyl-; 1,3-cyclohexanedione, 2-propanoyl-5-[4-fluorophenyl]-; 1,3-cyclohexanedione, 2-acetyl-5-[thien-2-yl]-; 1,3-cyclohexanedione, 2-acetyl-5-butyl-; and 1,3-cyclohexanedione, 2-propanoyl-5-[bicyclo[2.2.1]hept-2-en-5-yl]-. The compounds can be used to alter the lifespan of eukaryotic organisms and treat inflammation.

13 Claims, 8 Drawing Sheets

(56) References Cited

U.S. PATENT DOCUMENTS 5,089,046 A 2/1992 Lee et al.
5,744,648 A 4/1998 Elango et al.
2009/0163545 A1 6/2009 Goldfarb

OTHER PUBLICATIONS

Acne Health (2006).*

* cited by examiner

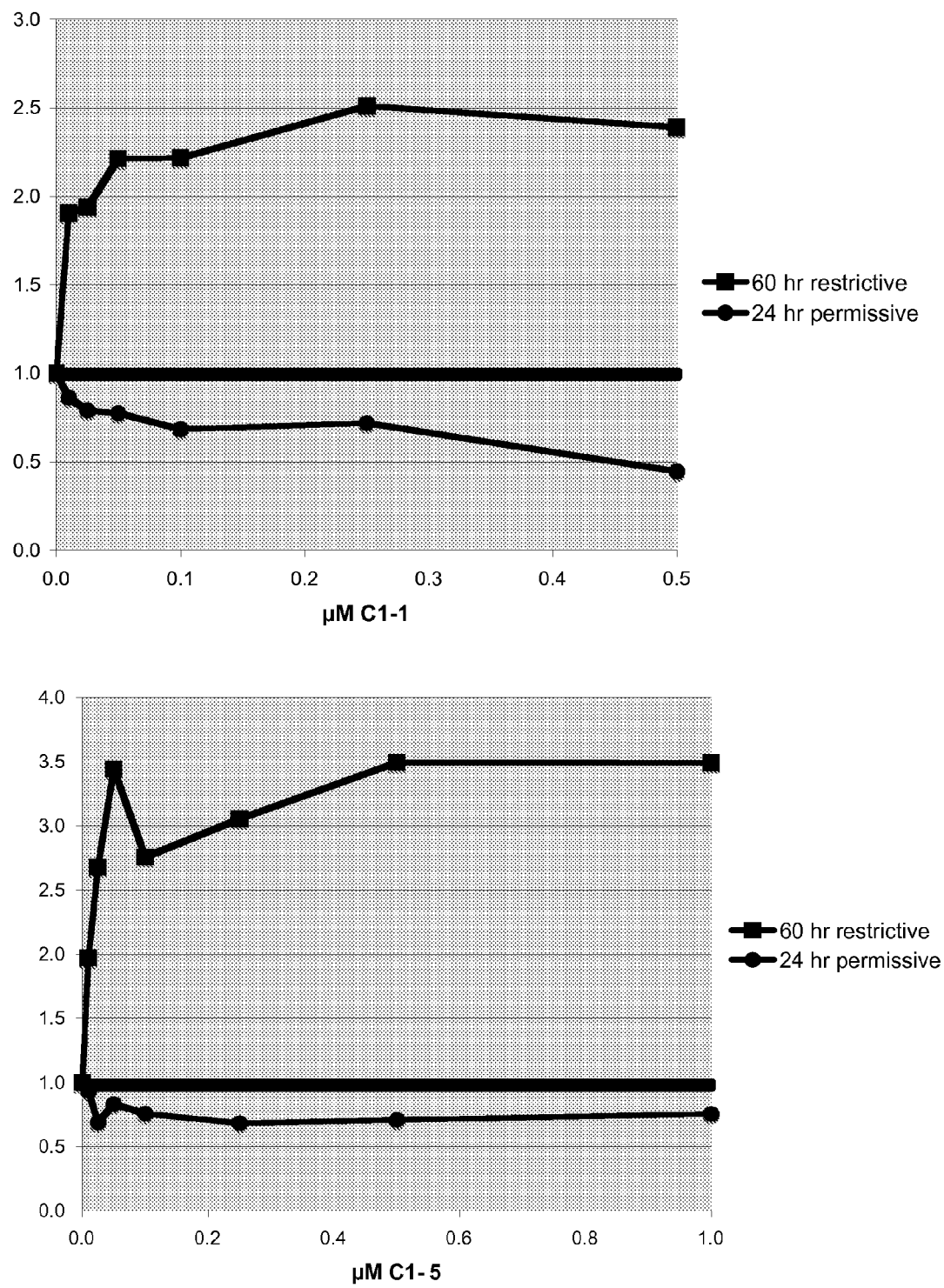
Figure 1A(1) and Figure 1A(2).

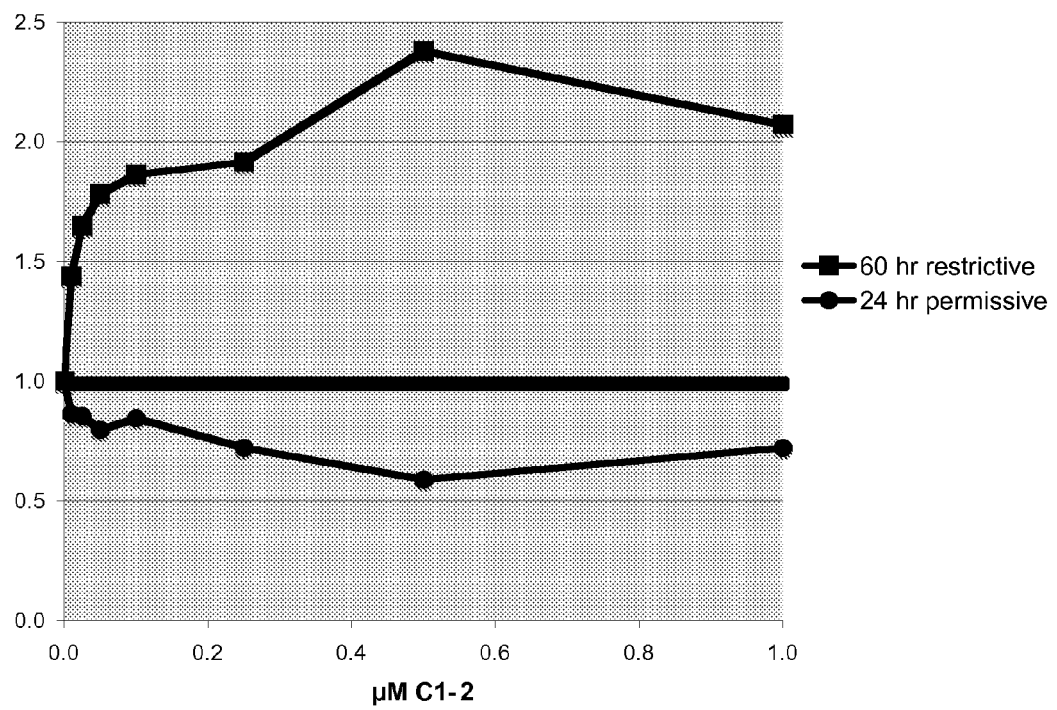
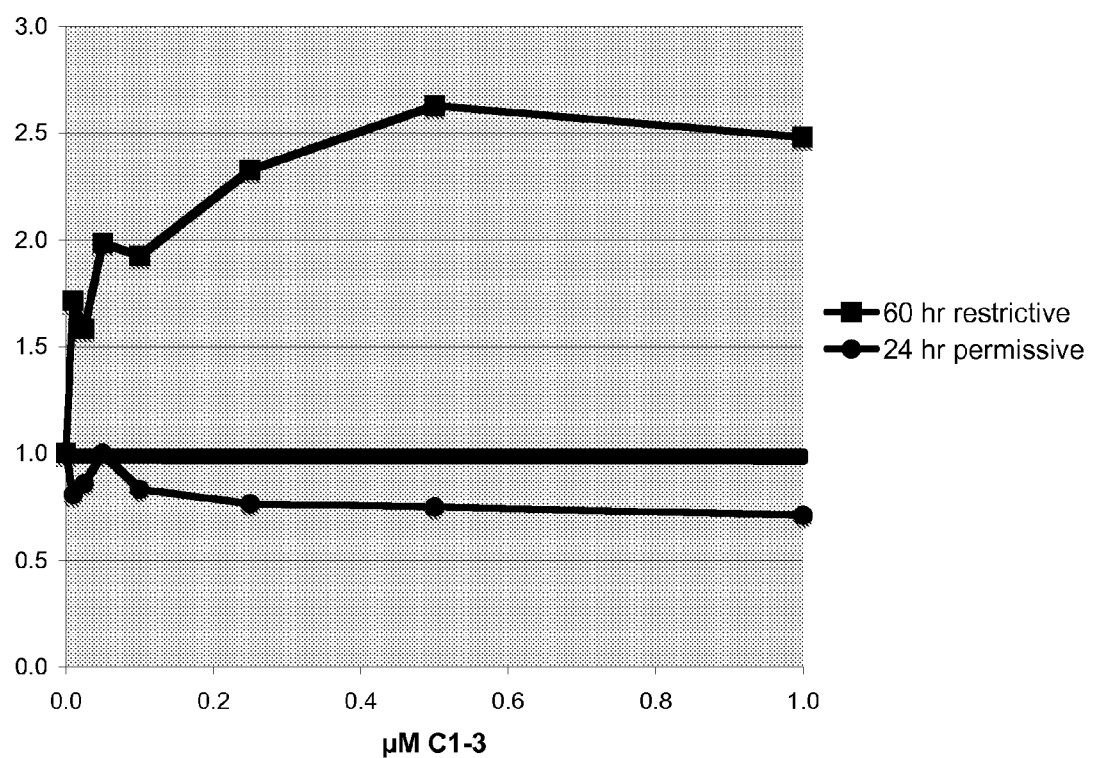
Figure 1A(3) and Figure1A(4)

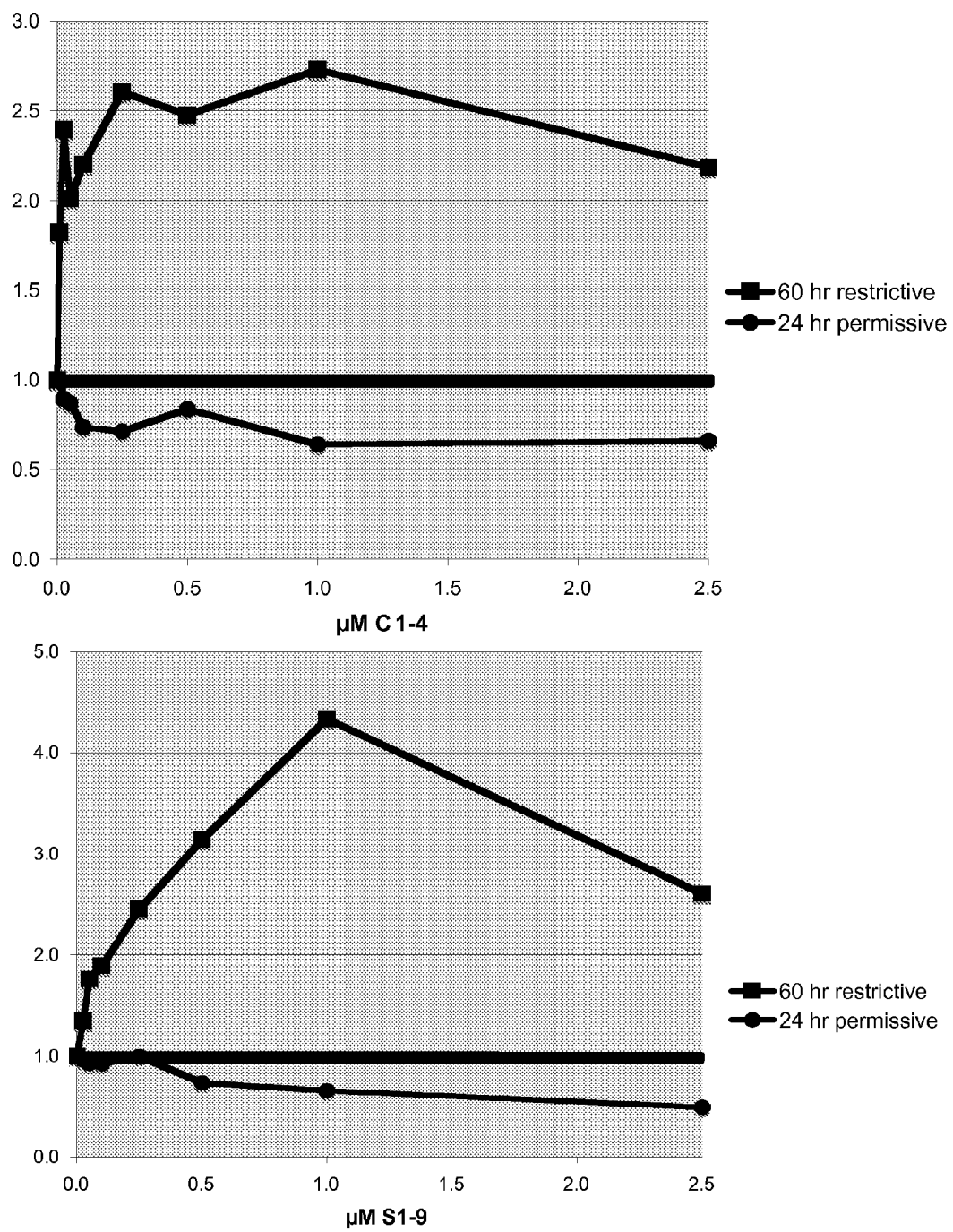
Figure 1A(5) and Figure 1A(6)

COMPOUNDS AND METHODS FOR ALTERING LIFESPAN OF EUKARYOTIC ORGANISMS

CROSS-REFERENCE TO RELATED APPLICATIONS

This application claims priority to U.S. provisional patent application No. 61/261,851, filed Nov. 17, 2009, the disclosure of which is incorporated herein by reference.

STATEMENT REGARDING FEDERALLY SPONSORED RESEARCH

This invention was made with government support under contract no. U54-HG-003917 awarded by the National Science Foundation. The government has certain rights in the invention.

FIELD OF THE INVENTION

The present invention generally relates to compounds and methods for altering the lifespan of eukaryotic organisms. More particularly, the present invention relates to triketone compounds and methods of using these compounds for altering the lifespan of eukaryotic organisms.

BACKGROUND OF THE INVENTION

There is an ongoing need for compositions and methods for altering the lifespan of eukaryotic cells and organisms. Dietary restriction (DR), also referred to as caloric restriction, has been proposed as one mechanism for altering the lifespan of eukaryotes. DR involves underfeeding short of malnutrition. DR regimens extend lifespan in eukaryotes from yeast to mammals by conserved genetic mechanisms, and delay the onset of age-related diseases such as diabetes, metabolic disorders, neurodegenerative diseases, cardiovascular diseases and cancer (Masoro, E, J. 2005. Overview of caloric restriction and ageing. Mech. Age. Dev. 126:913-922.; Morley, J. E., Chahla, E. Alkaade, S. (2010) Antiaging, longevity and caloric restriction. Curr. Opin. Clin, Nutr. Metab. Care. 13:40-45.). Optimal DR diets have not been determined for any organism, and it is likely that reducing specific nutrients within these diets, such as certain amino acids, may play disproportionate roles in achieving the full therapeutic benefits of DR. DR mimetics are a hypothetical class of drug that induce the beneficial affects of DR without altering diet.

Though the cellular mechanism(s) through which DR regimens exert their benefits are not well understood, their potential therapeutic value to humans has generated considerable interest. Studies have been extended to primates where it was shown that Rhesus monkeys kept for years on a DR regimen exhibit significantly fewer age-related diseases than animals kept on a normal diet (Colman, R. J., Anderson, R. M., Johnson, S. C., Kastman, E. K., Kosmatka, K. J., Beasley, T. M., Allison, D. B., Cruzen, C., Simmons, H. A., Kemnitz, J. W., Weindruch, R. (2009) Caloric restriction delays disease onset and mortality in rhesus monkeys. Science. 325:201-4.).

DR likely acts at least in part by reducing levels of deleterious reactive oxygen species (ROS). The long-term production of ROS in various tissues leads to chronic inflammation, tissue damage and, ultimately, age-related diseases (Chung, H. Y. et al. 2009. Molecular Inflammation Underpinnings of aging and age-related diseases. Ageing Research Rev. 8:18-30.). It is likely that many, if not all, bona fide DR mimetics will have anti-inflammatory activity. In contrast, not all anti-inflammatory drugs will exhibit DR mimetic activity. Thus DR mimetics may be active against any disease or disorder that has an inflammatory component, including those not necessarily associated with aging. However, there remains an ongoing and unmet need for DR mimetics for use in extending life span and for therapy and/or prophylaxis of inflammation.

BRIEF SUMMARY OF THE INVENTION

In an aspect, the present invention provides a compound with the following structure:

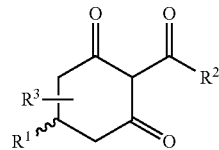

where $R^1$ and $R^2$ are independently selected from an aliphatic alkyl group having 1 carbon to 8 carbons, where the aliphatic alkyl group is linear or branched, saturated or has one or more carbon-carbon multiple bonds, and is, optionally, substituted with one or more halogens, a cyclic alkyl group having 3 carbons to 8 carbons, where the cyclic alkyl group is saturated or has one or more carbon-carbon multiple bonds, and is, optionally, substituted with one or more alkyl groups having 1 carbon to 6 carbons, an aryl group, where the aryl group has a single, multiple-ring or fused-ring structure, and each ring is, optionally, independently substituted with one or more groups selected from halogen, hydroxy, and alkoxy group having 1 carbon to 6 carbons, where if the compound is substituted with two adjacent alkoxy groups the groups are, optionally, linked by an alkyl group having 1 carbon to 4 carbons, amino group, alkylamino group having one alkyl group or two alkyl groups, wherein each alkyl group has 1 carbon to 6 carbons, arylamino group having one aromatic group or two aromatic groups, wherein each aryl group has 4 carbons to 6 carbons, alkyloxy group, wherein the alkyl group has 1 carbon to 6 carbons and is linear, branched or cyclic, and aryloxy group, wherein the aryl group has 4 carbons to 6 carbons, an aralkyl group, where the araalkyl group is attached via the aliphatic moiety having 1 carbon to 8 carbons and an aromatic moiety having 4 carbons to 8 carbons, or a heterocyclic group having 3 carbons to 8 carbons, wherein the heterocyclic group is saturated or comprises one or more carbon-carbon multiple bonds, and wherein $R^3$ is an optional substitution and is any of the $R^1$ and $R^2$ groups.

In an embodiment, the compound has one of the following structures:

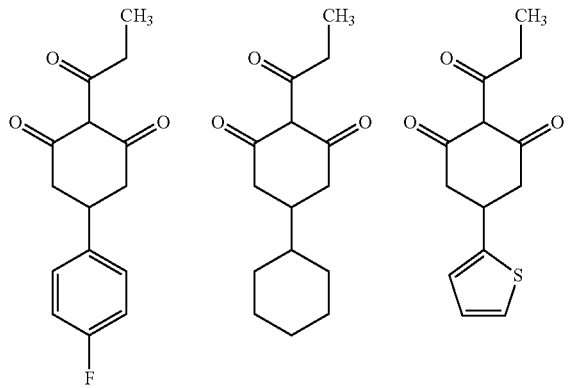

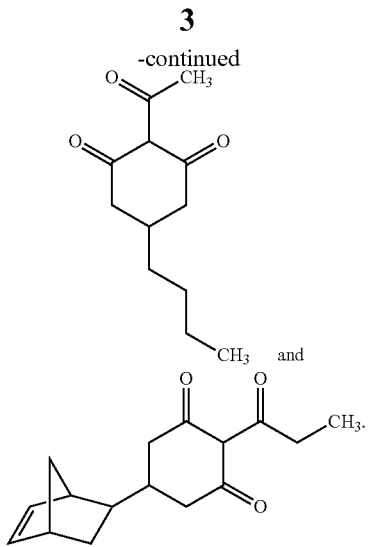

In an embodiment, the compound is selected from the compounds listed in Table 1.

In an aspect, the present invention provides a method for altering the lifespan of a eukaryotic organism comprising administering a composition comprising a compound of the present invention to the organism, where the lifespan of the eukaryotic organism is altered subsequent to the administration. For example, altering of the lifespan is extending the lifespan of the organism.

In another aspect, the present invention provides a method for prophylaxis and/or therapy of inflammation in an individual comprising administering a composition comprising a compound of the present invention to the individual, where inflammation in the organism is reduced subsequent to the administration. In one embodiment, the inflammation is positively correlated with an age-related disease.

BRIEF DESCRIPTION OF THE FIGURES

FIGS. 1A(1-6). Examples of lifespan altering effect of compounds of present invention.

DETAILED DESCRIPTION OF THE INVENTION

Figure 1B:
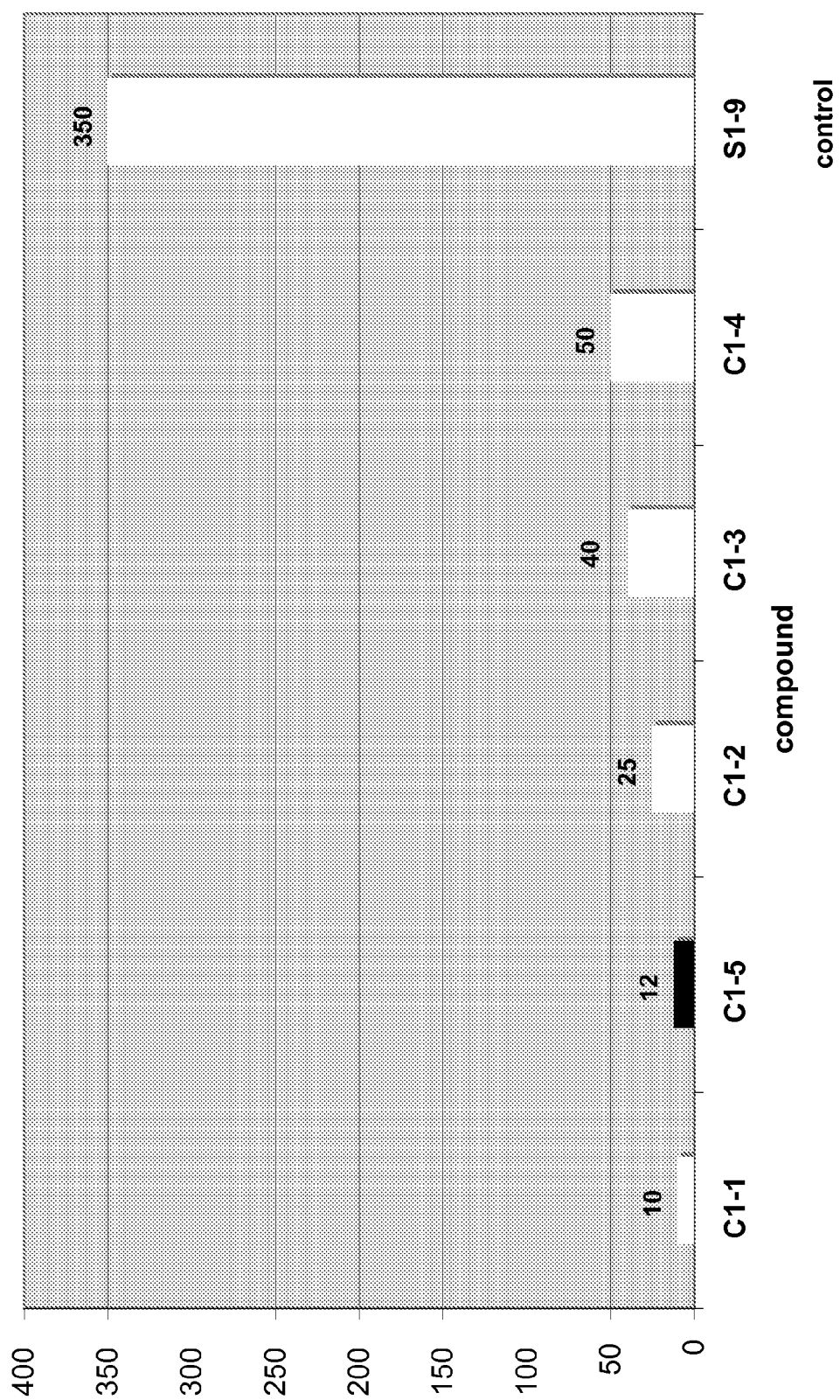
FIG. 1B. Examples of lifespan altering effect of compounds of present invention.

The present invention provides compounds and methods for altering the lifespan of eukaryotic organisms. The compounds of the present invention have a triketone chemical structure represented below in Formula 1.

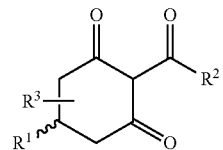

Formula 1 wherein $R^1$ and $R^2$ can independently be aliphatic alkyl, cyclic alkyl, aryl, aralkyl, or heterocyclic groups. These groups can be substituted or functionalized. The cyclohexanedione nucleus of this structure can be optionally substituted at an additional position on the cyclohexane ring by $R^3$. $R^3$ can be any of the aforementioned groups. Examples of compounds of the present invention are listed in Table 1 of Example 3.

The compound can have any stereochemistry. For example, the orientation of the $R^1$ substituent can be such that a specific entantiomer or diastereomer is formed. The present invention provides all possible enantiomers or diastereomers and mixtures thereof.

The aliphatic alkyl group has up to 12 carbons. For example, the group can have 1 carbon to 8 carbons. The group is branched or unbranched. The group is saturated or has one or more carbon-carbon multiple bonds. The aliphatic alkyl group can, optionally, be substituted. For example, the alkyl group can be substituted with one or more halogens (i.e, fluorine, chloride, bromide and iodide). Examples of aliphatic alkyl groups include, but are not limited to, n-butyl, 2-fluorobutyl, 3-ethylthiobutyl and the like.

The cyclic alkyl group has up to 12 carbons. For example, the group can have a ring containing from 3 carbons to 8 carbons. The cyclic alkyl group is saturated or has one or more carbon-carbon multiple bonds. The cyclic alkyl group can, optionally, be substituted. For example, the group can be substituted with one or more alkyl groups having 1 carbon to 6 carbons. Examples of cyclic alkyl groups include, but are not limited to, cyclohexyl, 2-methylcyclopentyl, 3-aminocyclobutyl and the like.

The aryl group contains an aromatic ring, or multiple-ring or fused-ring structures. The aryl group can, optionally, be substituted. For example, each ring can be independently substituted with one or more groups selected from halogen, hydroxy, alkoxy group having 1 carbon to 6 carbons, amino group, alkylamino group having one alkyl group or two alkyl groups, where each alkyl group independently has 1 carbon to 6 carbons, arylamino group having one aromatic group or two aromatic groups, where each group has 4 carbons to 6 carbons, alkylarylamino group having an alkyl group, where the alkyl group has 1 carbon to 6 carbons, and an aryl group, where the aromatic group has 4 carbons to 6 carbons, and alkyloxy group, where the alkyl moiety of the alkoxy group has 1 carbon to 6 carbons, and is linear, branched, or cyclic. The alkyl and aryl substitution groups can be further substituted. If the compound has an aryl group substituted with two adjacent alkoxy groups, the alkoxy groups can, optionally, be linked by an alkyl group having 1 carbon to 4 carbons. A phenyl ring is an example of an aromatic ring structure. A naphthyl group is an example of a fused-ring structure. Examples of aryl groups include, but are not limited to, phenyl, 3-trifluoromethylphenyl, naphthyl and the like. In one embodiment, $R^1$ is not a substituted phenyl group.

The aralkyl group has an aliphatic component (having 1 carbon to 8 carbons) and an aromatic component (having a 4 carbon to 14 carbon aromatic ring or rings) bonded to the cyclohexanedione nucleus through the aliphatic component. Examples of aralkyl groups include, but are not limited to, benzyl, 4-hydroxybenzyl, 3-iodobenzyl, 4-methoxyphenylethyl and the like.

The heterocyclic group has up to 10 carbons, and additionally has a heteroatom (such as oxygen, nitrogen and sulfur) as part of the ring structure. For example, the group can have 3 carbons to 8 carbons. The group is saturated or has one or more carbon-carbon multiple bond(s). The group can, optionally, be substituted. Examples of heterocyclic groups include, but are not limited to, thienyl, benzothiophen-2-yl, indol-3-yl, 3-pyridyl, furfuryl, 2-oxo-4-piperidinyl, and the like.

In an embodiment, the compound has the following structure:

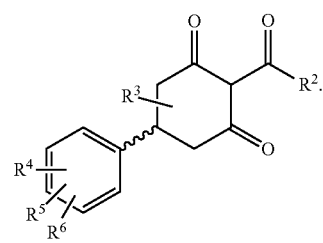

The compound comprises at least one of $R^4$, $R^5$ and $R^6$, and $R^4$, $R^5$ and $R^6$ are independently selected from halogen, hydroxy, alkoxy group having 1 carbon to 6 carbons, amino group, alkylamino group having one alkyl group or two alkyl groups, where each alkyl group independently has 1 carbon to 6 carbons, arylamino group having one aromatic group or two aromatic groups, where each group has 4 carbons to 6 carbons, alkylarylamino group having an alkyl group, where the alkyl group has 1 carbon to 6 carbons, and an aryl group, where the aromatic group has 4 carbons to 6 carbons, and alkyloxy group where the alkyl group has 1 carbon to 6 carbons and is linear, branched, cyclic and aryloxy group having 4 carbons to 6 carbons. If the compound is substituted with an aryl group having two adjacent alkoxy groups, the alkoxy groups are, optionally, linked by an alkyl group having from 1 carbon to 4 carbons.

In the preceding embodiment, the compound can have one of the following structures:

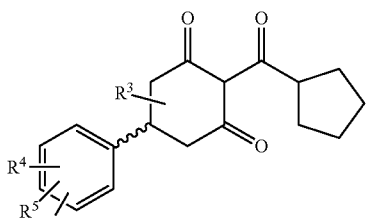

or

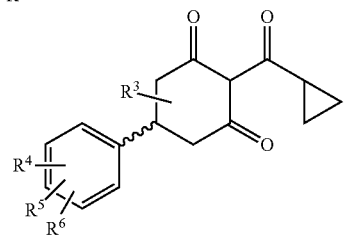

In another embodiment, the compound can have the following structure:

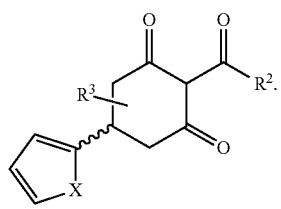

X is O, N, or S.

In the preceding embodiment, the compound can have one of the following structures:

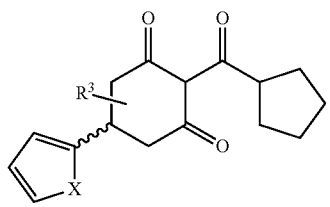

or

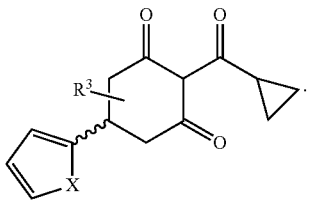

In another embodiment, the compound can have the following structure:

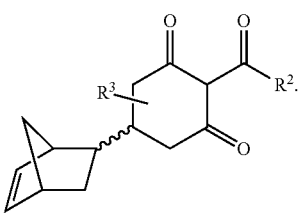

In another embodiment, the compound can have the following structure:

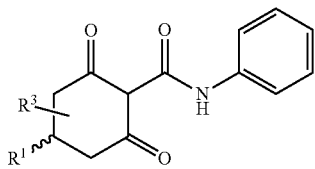

In the preceding embodiment, the compound can have one of the following structures:

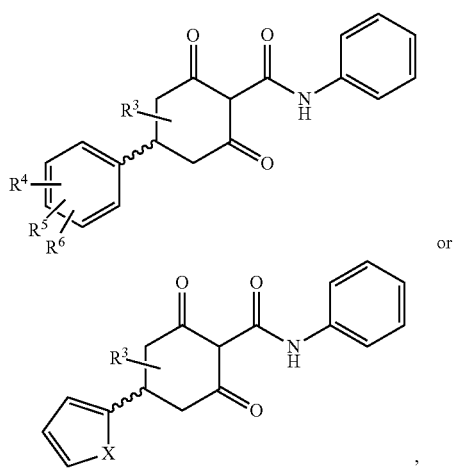

where X is O, N or S.

In another embodiment, the compound can have one of the following structures:

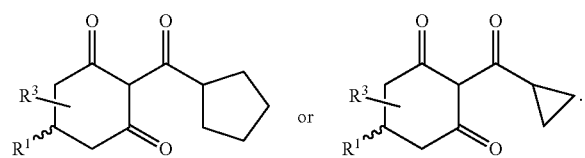

In an embodiment, for the structures herein depicting an $R^3$ substituent on the cyclohexyl ring, the present invention provides compounds having such structures where there is no $R^3$ substituent on the cyclohexyl ring.

In any of the instances where a maximum number of or range of a carbon atoms is set out in this application, such reference is intended to disclose every individual number of carbon atoms up to the stated maximum or within the stated range. For example, in the case of an alkyl group having up to 10 carbons, the alkyl group can have any number of carbon atoms from 1 to 10 carbons, e.g., 1, 2, 3, 4, 5, 6, 7, 8, 9 or 10. As another example, in the case on an alkyl group having 1 carbon to 8 carbons, the alkyl group can have any number of carbon atoms from 1 to 8 carbons, e.g., 1, 2, 3, 4, 5, 6, 7 or 8.

Examples of compounds of the present invention (which are listed in Table 1) include, but are not limited to: 1,3-cyclohexanedione, 2-acetyl-5-[4-(N,N-dimethylamino)phenyl]-; 1,3-cyclohexanedione, 2-cyclopentanecarbonyl-5-[4-methylphenyl]-; 1,3-cyclohexanedione, 2-cyclopentanecarbonyl-5-[4-(1-methylethyl)phenyl]-; 1,3-cyclohexanedione, 2-cyclopentanecarbonyl-5-[4-chlorophenyl]-; 1,3-cyclohexanedione, 2-cyclopentanecarbonyl-5-[fur-2-yl]-; 1,3-cyclohexanedione, 2-isobutyryl-5-[fur-2-yl]-; 1,3-cyclohexanedione, 2-benzoyl-5-[2-chloro-6-fluorophenyl]-; 1,3-cyclohexanedione, 2-propanoyl-5-[4-methoxyphenyl]-; 1,3-cyclohexanedione, 2-acetyl-5-[3,4-dimethoxyphenyl]-; 1,3-cyclohexanedione, 2-benzoyl-5-[3,4-dimethoxyphenyl]-; 1,3-cyclohexanedione, 2-acetyl-5-[naphth-2-yl]-; 1,3-cyclohexanedione, 2-benzoyl-5-[2,4-dichlorophenyl]-; 1,3-cyclohexanedione, 2-propanoyl-5-[2,4,5-trimethoxyphenyl]-; 1,3-cyclohexanedione, 2-benzoyl-5-[4-fluorophenyl]-; 1,3-cyclohexanedione, 2-benzoyl-5-[4-methoxyphenyl]-; 1,3-cyclohexanedione, 2-benzoyl-5-[fur-2-yl]-; 1,3-cyclohexanedione, 2-cyclopropanecarbonyl-5-[4-methoxyphenyl]-; 1,3-cyclohexanedione, 2-cyclopentanecarbonyl-5-[4-methoxyphenyl]-; 1,3-cyclohexanedione, 2-isobutyryl-5-[4-methoxyphenyl]-; 1,3-cyclohexanedione, 2-cyclopentanecarbonyl-5-phenyl-; 1,3-cyclohexanedione, 2-cyclopropanecarbonyl-5-[4-(N,N-dimethylamino)phenyl]-; 1,3-cyclohexanedione, 2-cyclopentanecarbonyl-5-[4-(N,N-dimethylamino)phenyl]-; 1,3-cyclohexanedione, 2-isobutyrylyl-5-[4-(N,N-dimethylamino)phenyl]-; 1,3-cyclohexanedione, 2-cyclopropanecarbonyl-5-[2,4,6-trimethylphenyl]-; 1,3-cyclohexanedione, 2-isobutyryl-5-[2,4,6-trimethylphenyl]-; 1,3-cyclohexanedione, 2-cyclopropanecarbonyl-5-[3,4-dimethoxyphenyl]-; 1,3-cyclohexanedione, 2-cyclopentanecarbonyl-5-[3,4-dimethoxyphenyl]-; 1,3-cyclohexanedione, 2-isobutyryl-5-[3,4-dimethoxyphenyl]-; N,5-diphenylcyclohexane-1,3-dione-2-carboxamide; N-phenyl-5-[4-fluorophenyl]-cyclohexane-1,3-dione-2-carboxamide; N-phenyl-5-[2,4-dichlorophenyl]-cyclohexane-1,3-dione-2-carboxamide; N-phenyl-5-[fur-2-yl]-cyclohexane-1,3-dione-2-carboxamide; N-phenyl-5-[2,4,6-trimethylphenyl]-cyclohexane-1,3-dione-2-carboxamide; N-phenyl-5-[3,4-dimethoxyphenyl]-cyclohexane-1,3-dione-2-carboxamide; 1,3-cyclohexanedione, 2-cyclopropanecarbonyl-5-[4-(cyclopropanecarboxy)phenyl]-; 1,3-cyclohexanedione, 2-propanoyl-5-methyl-; 1,3-cyclohexanedione, 2-acetyl-5-methyl-; 1,3-cyclohexanedione, 2-propanoyl-5-[indol-3-yl]-; 1,3-cyclohexanedione, 2-propanoyl-5-ethyl-; 1,3-cyclohexanedione, 2-butyryl-5-[4-hydroxyphenyl]-; 1,3-cyclohexanedione, 2-propanoyl-5-cyclohexyl-; 1,3-cyclohexanedione, 2-propanoyl-5-[2-chloro-6-fluorophenyl]-; 1,3-cyclohexanedione, 2-propanoyl-5-[4-fluorophenyl]-; 1,3-cyclohexanedione, 2-propanoyl-5-[fur-2-yl]-; 1,3-cyclohexanedione, 2-cyclopropanecarbonyl-5-[2,4,6-trimethoxyphenyl]-; 1,3-cyclohexanedione, 2-cyclopentanecarbonyl-5-[2,4,6-trimethoxyphenyl]-; 1,3-cyclohexanedione, 2-isobutyryl-5-[2,4,6-trimethoxyphenyl]-; 1,3-cyclohexanedione, 2-cyclopropanecarbonyl-5-[4-methylphenyl]-; 1,3-cyclohexanedione, 2-isobutyryl-5-[4-methylphenyl]-; 1,3-cyclohexanedione, 2-isobutyryl-5-[4-(1-methylethyl)phenyl]-; 1,3-cyclohexanedione, 2-cyclopropanecarbonyl-5-[4-chlorophenyl]-; 1,3-cyclohexanedione, 2-isobutyryl-5-[4-chlorophenyl]-; 1,3-cyclohexanedione, 2-cyclopropanecarbonyl-5-[fur-2-yl]-; 1,3-cyclohexanedione, 2-cyclopropanecarbonyl-5-[4-fluorophenyl]-; 1,3-cyclohexanedione, 2-cyclopentanecarbonyl-5-[4-fluorophenyl]-; 1,3-cyclohexanedione, 2-isobutyryl-5-[4-fluorophenyl]-; 1,3-cyclohexanedione, 2-propanoyl-5-[2,4-dichlorophenyl]-; 1,3-cyclohexanedione, 2-acetyl-5-[2,4-dichlorophenyl]-; 1,3-cyclohexanedione, 2-butyryl-5-[fur-2-yl]-; 1,3-cyclohexanedione, 2-benzoyl-5-cyclohexyl-; 1,3-cyclohexanedione, 2-acetyl-5-[2-chloro-6-fluorophenyl]-; 1,3-cyclohexanedione, 2-acetyl-5-[fur-2-yl]-; 1,3-cyclohexanedione, 2-acetyl-5-[4-fluorophenyl]-; 1,3-cyclohexanedione, 2-propanoyl-5-[4(N,N-dimethylamino)phenyl]-; 1,3-cyclohexanedione, 2-acetyl-5-[bicyclo[2.2.1]hept-2-en-5-yl]-; 1,3-cyclohexanedione, 2-propanoyl-5-[(3,4-ethylenedioxy)phenyl]-; 1,3-cyclohexanedione, 2-cyclopropanecarbonyl-5-phenyl-; 1,3-cyclohexanedione, 2-isobutyryl-5-phenyl-; 1,3-cyclohexanedione, 2-cyclopropanecarbonyl-5-[2,4-dichlorophenyl]-; 1,3-cyclohexanedione, 2-isobutyryl-5-[2,4-dichlorophenyl]-; 1,3-cyclohexanedione, 2-cyclopropanecarbonyl-5-[thien-2-yl]-; 1,3-cyclohexanedione, 2-isobutyryl-5-[thien-2-yl]-; 1,3-cyclohexanedione, 2-acetyl-5-hexyl-; 1,3-cyclohexanedione, 2-propanoyl-5-hexyl-; 1,3-cyclohexanedione, 2-propanoyl-5-[thien-2-yl]-; 1,3-cyclohexanedione, 2-acetyl-5-(1-methylethyl)-; 1,3-cyclohexanedione, 2-propanoyl-5-(1-methylethyl)-; 1,3-cyclohexanedione, 2-acetyl-5-[thien-2-yl]-; 1,3-cyclohexanedione, 2-acetyl-5-[4-hydroxyphenyl]-; 1,3-cyclohexanedione, 2-acetyl-5-[3,4-methylenedioxyphenyl]-; 1,3-cyclohexanedione, 2-propanoyl-5-[3,4-methylenedioxyphenyl]-; 1,3-cyclohexanedione, 2-acetyl-5-[3,4-ethylenedioxyphenyl]-; 1,3-cyclohexanedione, 2-acetyl-5-[N-methylindol-3-yl]-; 1,3-cyclohexanedione, 2-acetyl-5-ethyl-; 1,3-cyclohexanedione, 2-acetyl-5-butyl-; 1,3-cyclohexanedione, 2-propanoyl-5-butyl-; 1,3-cyclohexanedione, 2-acetyl-5-pentyl-; 1,3-cyclohexanedione, 2-propanoyl-5-pentyl-; 1,3-cyclohexanedione, 2-butyryl-5-[N-methylindol-3-yl]-; and 1,3-cyclohexanedione, 2-propanoyl-5-[bicyclo[2.2.1]hept-2-en-5-yl]-.

Compounds of the present invention can be referred to alternatively by structure, chemical name, or by the designations set forth as compound numbers and SRI numbers in Tables 1 and 2, as well as the designations C1-1, C1-2, C1-3, C1-4, and C1-5 (see for instance Table 2, Example 4).

In an embodiment, the present invention provides a composition comprising one or more of the compounds disclosed herein. For example, the composition can be a pharmaceutical composition that can be used for administration to a cell or an individual using any suitable route. The composition can have, for example, one or more excipients, binding agents, or other compounds, materials, agents, etc. that would be recognized by one having skill in the art as needed to prepare the desired composition.

The compounds of the present invention can be synthesized, for example, by the following general procedure:

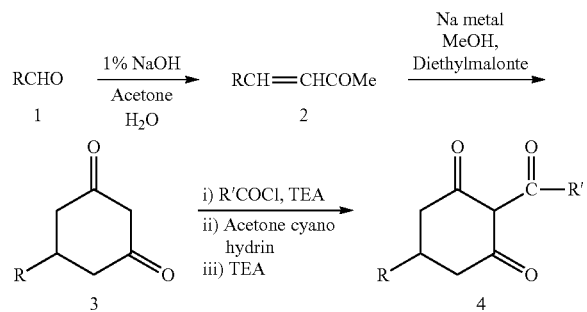

Intermediate 2 is prepared from an aldehyde (1) and a ketone such as acetone by base-catalyzed condensation, followed by cyclization with dimethylmalonate to afford intermediate 3 according to the procedure of Yoshihiko Yoshimoto et al. (*J. Med. Chem.* 1977, 20, 709-714). Compound 3 in dry $CH_2Cl_2$ is treated with an acid chloride and triethylamine, stirred at ambient temperature for 1.5 hours, then evaporated to dryness, taken up in acetonitrile, treated with acetone cyanohydrin and triethylamine. The reaction mixture is stirred for 18 hours and evaporated to dryness. Column chromatography affords the desired pure final product 4.

The compounds of the present invention can be used to alter lifespan in eukaryotic organisms. Examples of eukaryotic organisms suitable for receiving the compositions comprising the compounds of the invention include single- and multi-cellular organisms, and higher-order organisms (such as mammals, which include humans). The compounds of the invention were found to affect lifespan in animal models such as *S. cerevisiae* ("yeast"), *C. elegans* worms, and *D. melanogaster* flies which indicates that the compounds will have similar effects in in higher eukaryotic organisms such as humans. It is also contemplated that the invention will be useful for altering the lifespan of various animals for veterinary/and or agricultural purposes, such as for extending the lifespan of domesticated animals that are used for companionship, including, but not limited to, felines and canines, and/or animals used for food or other material production including, but not limited to, cattle, poultry and fish, and/or for those that are maintained in captivity for scientific, research and/or educational purposes, including, but not limited to, non-human primates and all other animals that are subject to animal husbandry.

In an embodiment, the invention comprises a method for prophylaxis and/or therapy of acute and/or chronic inflammation in an individual. The method comprises administering to an individual a composition comprising one or more of the compounds disclosed herein, wherein inflammation in the individual is inhibited and/or reduced via administration of the composition. A reduction in inflammation can be evidenced by a reduction in the production of any of various well known markers of inflammation (see, for example, Carl Nathan, Points of control in inflammation, Nature (2002), Vol. 420, p 846-852), such as a reduction in interleukins and/or cytokines typically associated with inflammation, TNFα, MCP-1 and/or total Europhiles in an area where inflammation would be expected due to an environmental insult, such as cigarette smoke in the lungs.

In an embodiment, the individual to whom a composition comprising one or more of the compounds disclosed herein is administered is an individual who is at risk for, is suspected of having, or is diagnosed with a disorder that is caused by and/or is positively correlated with abnormal and/or undesirable inflammation. In one embodiment, the inflammation is positively correlated with an age-related disease.

In one embodiment, the present invention provides a method for altering the lifespan of a eukaryotic organism. The method comprises administering a composition comprising a lifespan altering compound to a eukaryotic organism, such that the lifespan of the eukaryotic organism is altered.

The term "lifespan" as used herein means the number of times a cell or cell population can divide (explicative lifespan) or the length of time (e.g. days or years) a cell or organism survives before dying (chronological lifespan). Accordingly, the compounds of the present invention are referred to as lifespan altering compounds (Laces). The term LAC includes, but is not limited to, compounds that are prophylactic and/or therapeutic for inflammation in an individual.

Without intending to be bound by any particular theory, it is considered that a LAC may alter the lifespan through CR, dietary restriction (DR), or some other pathway.

The Laces can alter the lifespan of a eukaryotic organism by reversing the effect of a lifespan shortening agent (such as nicotinamide (NIC), or paraquat—an environmental agent), or it can increase the lifespan of the eukaryotic organism which has or has not been exposed to a lifespan shortening agent. Examples of lifespan altering activity include, but are not limited to: increasing the explicative lifespan of yeast cells in the DeaD assay; increasing the explicative lifespan of yeast cells in the presence or absence of a lifespan shortening agent (such as NIC); increasing the explicative lifespan of yeast cells in the presence or absence of an environmental agent (such as paraquat); increasing the lifespan of an higher organism such as *C. elegans* or *D. melanogaster*; or increasing the lifespan of a mammal such as a human.

In an embodiment, the present invention can cause the mammalian cells that are contacted with a composition comprising a compound of the invention to become quiescent. In an embodiment, prior to being becoming quiescent, the mammalian cells are senescent. Thus, the invention can be used to induce mammalian cells to become quiescent.

The C50 (50% maximal activity) is a measure of the efficacy of a compound as a LAC and is determined by quantifying the dose-response curve for each LAC by DeaD assay in the presence and absence of nicotinamide. The C50 is the concentration of LAC that yields half the maximal activity. Dose response curves will generally peak and then decline. The decline is most likely due to toxicity at higher LAC concentrations. The C50 is determined relative to the maximal lifespan extension (the peak value). C50 values are provided for C1-5.

An effective amount of a LAC alters (for example, increases or decreases) the lifespan of an eukaryotic organism. For example, an effective amount of a LAC increases the lifespan of an eukaryotic organism by a statistically significant amount compared to the lifespan of an untreated organism. The lifespan of an untreated organism may be determined in parallel or may be obtained from separately conducted studies (control). For example, an effective amount of a LAC alters the lifespan of an eukaryotic organism by at least 5% over control. In other embodiments, an effective amount of a LAC alters the lifespan of an eukaryotic organism by at least 10, 15, 20, 25, 35, 50%, or 100% over control.

It is expected that the compound can be delivered to a eukaryotic organism using any available method and route suitable for compound delivery, including oral, parenteral, subcutaneous, intraperitoneal, intrapulmonary, and intranasal routes. It will be recognized by those of skill in the art that the form and character of the particular dosing regimen employed in the method of the invention will be dictated by the route of administration and other well-known variables, such as the size and age of the eukaryotic organism. Determination of such dosing regimens is within the purview of one skilled in the art. Administration of the compound could be performed in conjunction with any conventional therapies that are intended to treat a disease or disorder associated with aging including topical, oral, or injectable. Administration of the LAC can also be done by exposing or contacting the cell or cells to an environment (such a growth or culture medium) containing an effective amount of a LAC.

In one embodiment, the present method can be used in order to generally increase the lifespan of the cells of a eukaryotic organism and to protect its cells against stress and/or against apoptosis. While not intending to be bound by any particular theory, it is believed that use of the present method is similar to subjecting the subject to hormesis, i.e., mild stress that is beneficial to organisms and may extend their lifespan.

In various other embodiments, the present method can be used for treating or preventing a disease or condition induced or exacerbated by cellular senescence in a subject; for extending the lifespan of a subject; for treating or preventing a disease or condition relating to lifespan; for treating or preventing a disease or condition relating to the proliferative capacity of cells; for treating or preventing a disease or condition resulting from cell damage or death.

For example, the present method may be used to prevent aging and aging-related consequences or diseases or inflammation associated with diseases that include but are not necessarily limited to stroke, heart disease, heart failure, arthritis, high blood pressure, and Alzheimer's disease. Other conditions that can be treated include ocular disorders, e.g., associated with the aging of the eye, such as cataracts, glaucoma, and macular degeneration. The present method may also be used to treat chronic diseases associated with cell death in order to protect the cells from cell death. Exemplary diseases include those associated with neural cell death, neuronal dysfunction, or muscular cell death or dysfunction, such as Parkinson's disease, Alzheimer's disease, multiple sclerosis, amniotropic lateral sclerosis, and muscular dystrophy; AIDS; fulminant hepatitis; diseases linked to degeneration of the brain, such as Creutzfeld-Jakob disease, retinitis pigmentosa and cerebellar degeneration; myelodysplasis such as aplastic anemia; ischemic diseases such as myocardial infarction and stroke; hepatic diseases such as alcoholic hepatitis, hepatitis B and hepatitis C; joint-diseases such as osteoarthritis; atherosclerosis; alopecia; damage to the skin due to UV light; lichen planus; atrophy of the skin; cataract; and graft rejections. Other causes of cell death include surgery, drug therapy, chemical exposure or radiation exposure.

The present method may also be used to treat acute diseases, e.g., damage to an organ or tissue, e.g., a subject suffering from stroke or myocardial infarction or a subject suffering from a spinal cord injury or may also be used to repair an alcoholic's liver.

In another embodiment, the invention provides a method extending the lifespan of a eukaryotic cell, extending the proliferative capacity of a eukaryotic cell, slowing ageing of a eukaryotic cell, promoting the survival of a eukarotic cell, delaying cellular senescence in a eukaryotic cell, mimicking the effects of calorie restriction, increasing the resistance of a eukaryotic cell to stress, or preventing apoptosis of a eukaryotic cell, by contacting the cell with a compound of the present invention.

For example, the present method may be used to increase the amount of time that eukaryotic cells, particularly primary eukaryotic cells (i.e., cells obtained from an organism, e.g., a human), may be kept alive in a cell culture. Embryonic stem (ES) cells and pluripotent cells, and cells differentiated therefrom, may also be treated with a compound of the present invention to keep the cells, or progeny thereof, in culture for longer periods of time. Such cells can also be used for transplantation into a subject, e.g., after ex vivo modification.

As another example, eukaryotic cells that are intended to be preserved for long periods of time may be treated using the method of the present invention. The cells may be in suspension (e.g., blood cells, serum, biological growth media, etc.) or in tissues or organs. For example, blood collected from an individual for purposes of transfusion or blood to be used for forensic activity may be treated using the present invention to preserve the blood cells for longer periods of time. Other cells that may be treated to extend their lifespan or protect against apoptosis include cells for consumption, e.g., cells from non-human mammals (such as meat) or plant cells (such as vegetables).

As yet another example, the method of the present invention may also be applied during developmental and growth phases in mammals, plants, insects or microorganisms, in order to, e.g., alter, retard or accelerate the developmental and/or growth process.

As yet another example, the present method can be used to treat cells useful for transplantation or cell therapy, including, for example, solid tissue grafts, organ transplants, cell suspensions, stem cells, bone marrow cells, etc. The cells or tissue may be an autograft, an allograft, a syngraft or a xenograft. The cells or tissue may be treated according to the present method prior to administration/implantation, concurrently with administration/implantation, and/or post administration/implantation into a subject. The cells or tissue may be treated prior to removal of the cells from the donor individual, ex vivo after removal of the cells or tissue from the donor individual, or post implantation into the recipient.

In yet another embodiment, cells may be treated using the method of the present invention to increase their lifespan or prevent apoptosis. For example, skin can be protected from aging (e.g., developing wrinkles, loss of elasticity, etc.) by treating skin or epithelial cells with the method of the present invention. Exemplary skin afflictions or skin conditions that may be treated in accordance with the methods described herein include disorders or diseases associated with or caused by inflammation, sun damage or natural aging. For example, the present method can find utility in the prevention or treatment of contact dermatitis (including irritant contact dermatitis and allergic contact dermatitis), atopic dermatitis (also known as allergic eczema), actinic keratosis, keratinization disorders (including eczema), epidermolysis bullosa diseases (including penfigus), exfoliative dermatitis, seborrheic dermatitis, erythemas (including erythema multiforme and erythema nodosum), damage caused by the sun or other light sources, discoid lupus erythematosus, dermatomyositis, psoriasis, skin cancer and the effects of natural aging. In another embodiment, the method of the present invention may be used for the treatment of wounds and/or burns to promote healing, including, for example, first-, second- or third-degree burns and/or a thermal, chemical or electrical burns.

The following non-limiting Examples provide further description of the present invention.

EXAMPLE 1

Preparation of Examples of Compounds of the Present Invention.

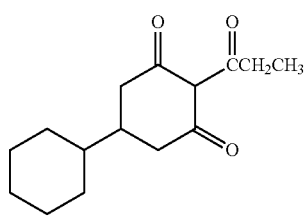

Compound I

Preparation of Compound I (41; SRI-22788). Cyclohexane carboxaldehyde (1; 40 mmol, 4.8 ml) was taken in acetone (6 ml), water (8 ml) and 1% NaOH (10 ml). This mixture was heated at 7° C. for 2.5 hours. The mixture was poured into $H_2O$ (100 ml) and extracted with chloroform which was evaporated to dryness to give an intermediate chalcone (2) (5.4 grams, 89% yield).

Sodium metal (1 molar equivalent (eq.), 800 mg) was dissolved in dry methanol (15 ml). After 0.5 hours, diethylmalonate (1 eq., 5.4 ml) was added dropwise to maintain a temperature between 15-20° C.; (2) is then added at 60° C. The reaction mixture was refluxed (80° C.) for 4 hours and made alkaline with aqueous NaOH (12.5 ml of 17.6 grams NaOH in 70 ml $H_2O$). The alkaline solution was heated at 80° C. for 40 minutes, and then concentrated HCl (12.5 ml) was added under reflux. On cooling, a yellow solid (3) was obtained (1.7 grams, 25% yield).

To (3) (1.76 grams, 9.07 ml) in methylene chloride (50 ml) was added propionyl chloride (1.1 eq.) and triethylamine (1.2 eq). This reaction mixture was stirred at room temperature for 1.5 hours then evaporated to dryness. The residue was taken up in acetonitrile, and acetone cyanohydrin (1 ml) was added followed by the addition of triethylamine (1 ml). After 18 hours, the reaction was evaporated. Compound I was obtained by column chromatography in chloroform and 1% methanol (62% yield). Analysis using mass spectrometry provided peaks with a m/z value corresponding to $[M+H]^+=251.17$ and $[M+Na]^+=273.15$.

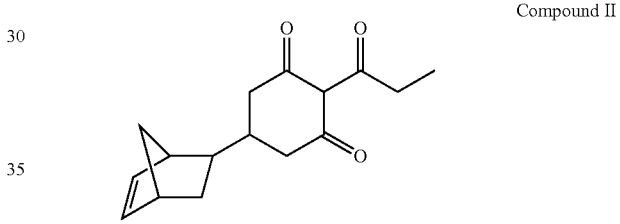

Compound II

Preparation of Compound II (90; SRI-22965). 5-norborene-2-carboxaldehyde (4; 40 mmol) was taken in acetone (6 ml), water (8 ml) and 1% NaOH (10 ml). This mixture was heated at 70° C. for 2.5 hours. The mixture was poured into $H_2O$ (100 ml) and extracted with chloroform which was evaporated to dryness to give an intermediate chalcone (5) (6.2 grams, 95% yield).

Sodium metal (1 eq.) was dissolved in dry MeOH (20 ml). After 0.5 hours, diethylmalonate (1 eq., 6.2 ml) was added dropwise to maintain temperature between 15-20° C.; (5) is then added at 60° C. The reaction mixture was refluxed (80° C.) for 4 hours and made alkaline with aqueous NaOH (13 hours of 17.6 grams NaOH in 70 ml $H_2O$). The alkaline solution was heated at 80° C. for 40 minutes, and then conc. HCl (13 ml) was added under reflux. On cooling, a yellow solid (6) was obtained (3.1 grams, 68% yield).

To (6) (1.6 grams) in methylene chloride (50 ml) was added propionyl chloride (1.1 eq.) and triethylamine (1.2 eq). This reaction mixture was stirred at room temperature for 1.5 hours, and then evaporated to dryness. The residue was taken up in acetonitrile, acetone cyanohydrin (1 ml) was added followed by the addition of triethylamine (1 ml). After 18 hours, the reaction was evaporated. Compound II was obtained by column chromatography in cyclohexane, ethylacetate (10-15%) 40% yield. Analysis using mass spectrometry provided peaks with a m/z value corresponding to $[M+H]^+=261.19$ and $[M+Na]^+=283.17$.

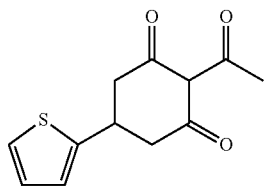

Compound III

Preparation of Compound III (78; SRI-22933). 2-Thiophenecarboxaldehyde (7; 40 mmol, 4.8 ml) was taken in acetone (6 ml), water (8 ml) and 1% NaOH (10 ml). This mixture was heated at 70° C. for 2.5 hours. The mixture was poured into H$_2$O (100 ml) and extracted with chloroform which was evaporated to dryness to give the intermediate chalcone (8) (6 grams, 99% yield).

Sodium metal (1 eq., 970 mg) was dissolved in dry MeOH (20 ml). After 0.5 hours, diethylmalonate (1 eq., 6.2 ml) was added dropwise to maintain temperature between 15-20° C.; (8) is then added at 60° C. The reaction mixture was refluxed (80° C.) for 4 hours and made alkaline with aqueous NaOH (13 ml of 17.6 grams NaOH in 70 ml H$_2$O). The alkaline solution was heated at 80° C. for 40 minutes, and then conc. HCl (13 ml) was added under reflux. On cooling, a yellow solid (9) was obtained (5.3 grams, 69% yield).

To (9) (1.7 grams) in methylene chloride (50 ml) was added acetyl chloride (1.1 eq.) and triethylamine (1.2 eq). This reaction mixture was stirred at ambient temperature for 1.5 hours, and then evaporated to dryness. The residue was taken up in acetonitrile, acetone cyanohydrin (1 ml) was added followed by the addition of triethylamine (1 ml). After 18 hours, the reaction was evaporated. Compound III was obtained by column chromatography in cyclohexane, ethylacetate (10-15%) 53% yield. Analysis using mass spectrometry provided peaks with a m/z value corresponding to [M+H]$^+$=237.10 and [M+Na]$^+$=259.09.

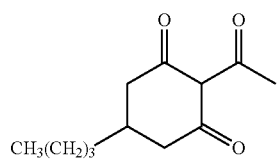

Compound IV

Preparation of Compound IV (85; SRI-22942). Valeraldehyde (10; 40 mmol, 4.8 ml) was taken in acetone (6 ml), water (8 ml) and 1% NaOH (10 ml). This mixture was heated at 70° C. for 2.5 hours. The mixture was poured into H$_2$O (100 ml) and extracted with chloroform which was evaporated to dryness to give the intermediate chalcone (11) (3.5 grams, 62% yield).

Sodium metal (1 eq., 600 mg) was dissolved in dry MeOH (13 ml). After 0.5 hours, diethylmalonate (1 eq., 5.4 ml) was added dropwise to maintain temperature between 15-20° C.; (11) is then added at 60° C. The reaction mixture was refluxed (80° C.) for 4 hours and made alkaline with aqueous NaOH (11 ml of 17.6 grams NaOH in 70 ml H$_2$O). The alkaline solution was heated at 80° C. for 40 minutes, and then conc. HCl (13 ml) was added under reflux. On cooling, a yellow oil (12) was obtained (3.5 grams, 70% yield).

To (12) (3.5 grams) in methylene chloride (50 ml) was added acetyl chloride (1.1 eq.) and triethylamine (1.2 eq). This reaction mixture was stirred at room temperature for 1.5 hours, and evaporated to dryness. The residue was taken up in acetonitrile, acetone cyanohydrin (1 ml) was added followed by the addition of triethylamine (1 ml). After 18 hours, the reaction was evaporated. Compound IV was obtained by column chromatography in cyclohexane, ethylacetate (10-15%) 15% yield. Analysis using mass spectrometry provided peaks with a m/z value corresponding to [M+H]$^+$=211.17 and [M+Na]$^+$=233.15.

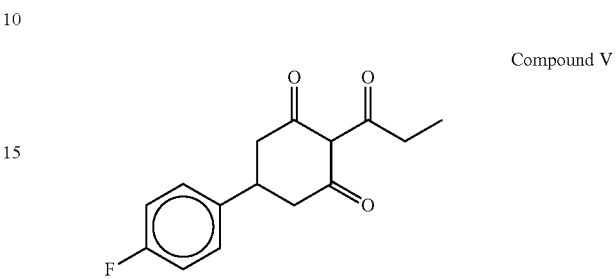

Compound V

Preparation of Compound V (43; SRI-22790). 4-Fluorobenzaldehyde (13; 40 mmol, 4.8 ml) was taken in acetone (6 ml), water (8 ml) and 1% NaOH (10 ml). This mixture was heated at 70° C. for 2.5 hours. The mixture was poured into H$_2$O (100 ml) and extracted with chloroform which was evaporated to dryness to give an intermediate chalcone (14) (6.5 grams, 98% yield).

Sodium metal (1 eq., 934 mg) was dissolved in dry methanol (13 ml). After 0.5 hours, diethylmalonate (1 eq., 6.2 ml) was added dropwise to maintain temperature between 15-20° C.; (14) is then added at 60° C. The reaction mixture was refluxed (80° C.) for 4 hours and made alkaline with aqueous NaOH (15 ml of 17.6 grams NaOH in 70 ml H$_2$O). The alkaline solution was heated at 80° C. for 40 minutes, and then conc. HCl (15 ml) was added under reflux. On cooling, a yellow oil (15) was obtained (47% yield).

To 15 (1.7 grams) in methylene chloride (50 ml) was added propionyl chloride (1.1 eq.) and triethylamine (1.2 eq). This reaction was stirred at room temperature for 1.5 hours, and evaporated to dryness. The residue was taken up in acetonitrile, acetone cyanohydrin (1 ml) was added followed by the addition of triethylamine (1 ml). After 18 hours, the reaction was evaporated. Compound V was obtained by column chromatography in cyclohexane, ethylacetate (10-15%) 70% yield. Analysis using mass spectrometry provided peaks with a m/z value corresponding to [M+H]$^+$=263.14 and [M+Na]$^+$=285.12.

EXAMPLE 2

Activity of Specific Compounds of the Present Invention in Yeast Dead Lifespan Assay.

The compounds listed in Table 1 of Example 3 were assessed for their anti-aging activities using the yeast Death of Daughters (DeaD) explicative lifespan assay. Specifically, the compounds were assessed for their capacity to reverse the lifespan shortening effect of exogenous nicotinamide (NAM), which is a known inhibitor of the anti-aging protein Sir2p (Anderson et al., 2003; Bitterman et al., 2002). These compounds were compared to the activities of known cluster 1 compounds, S3-5, and #3-11.

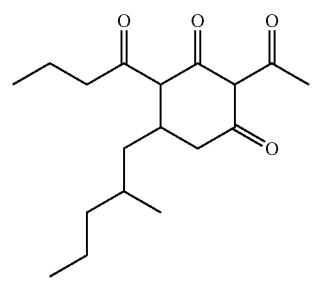

Compound 3-11

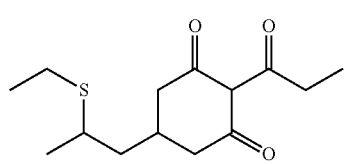

Compound S3-5

"Activity" here is defined herein as the fold improvement in DeaD lifespan in the presence of 0.75 mM NAM relative to lifespan in the absence of cluster 1 compounds, over a range of compound concentrations between 0.5 nm-1 μm. This "activity" value is a means of assessing the usefulness of a compound as a LAC. The assays were performed as follows. DeaD strain BB579 was grown overnight in a permissive (galactose-containing) medium to mid-log phase, and then diluted to an OD600 of 0.0001 in restrictive (glucose-containing) medium with 0.75 mM NAM and the compound to be tested. Cells were then incubated at 30° C. for 3 days, with shaking and OD600 measurement every 20 minutes. The OD600 reading after 60 hours in restrictive medium, normalized to the same measurement for the "no drug" control, was used as the number for comparison.

By this criterion, as summarized in Table 2 of Example 4, 17 of the 90 compounds showed higher activity than S3-5. 41 compounds showed activity similar to or less than compound S3-5, and 32 compounds showed little or no activity.

Five of the compounds with higher activity than S3-5 were selected for further study and were designated C1-1, C1-2, C1-3, C1-4, and C1-5 (see Table 2, Example 4). All data in FIGS. 1A(1)-(6) are from media containing 0.75 mM NAM. Note the different ranges of the X axes in FIGS. 1A(1)-(6)—very different C50 values for the compounds of the present invention compared the known C1 cluster compounds. (See the bar graph in FIG. 1B.) As shown in FIGS. 1A(1-6) and 1B all five of these compounds exhibited half maximal activities (C50) by DeaD assay at much lower concentrations than S3-5 (5-phenyl-2-propionyl-1,3-cyclohexanedione; Cambridge #5220071), a known cluster 1 compound. All five had C50 values below 50 nM, while the C50 value for S3-5 was about 650 nM, and the C50 for S1-9 was about 350 nM.

Toxicity of Compounds by Yeast Growth Assay.

Figure 2:
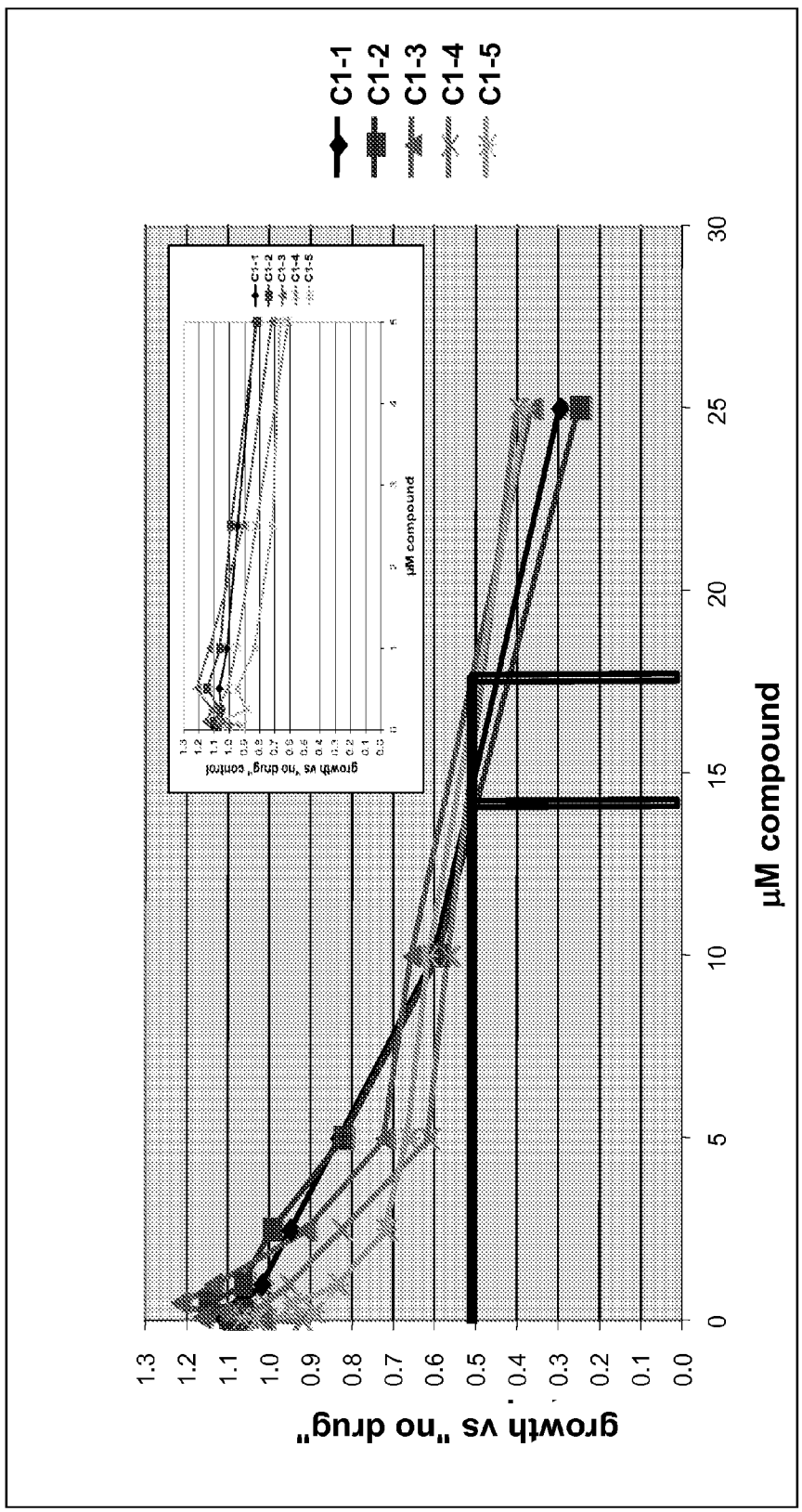
FIG. 2. Examples of lifespan altering effect of compounds of present invention.

The toxicity of compounds C1-1, C1-2, C1-3, C1-4, and C1-5 in yeast was assessed by determining their effects on growth of a wild-type yeast strain. FIG. 2 is a graphical representation of the toxicity data. The yeast used was strain FY839 (healthy wild-type) growing in SCD. At 12 hours all were in log phase. As shown in FIG. 2, the growth of the healthy parental yeast strain FY839 was reduced by half by concentrations of these five compounds of >10 μm. This concentration is many-fold higher than the effective concentrations of these compounds as assessed by DeaD lifespan assays. As shown in the inset in FIG. 2, compounds C1-1, C1-2, C1-3, and C1-4 show little or no toxic effects on growth at concentrations below 1 μM, which is ~50 times higher than their concentrations that yield half maximal activities (C50).

EXAMPLE 3

Examples of compounds of the present invention.

TABLE 1

| Compound No. | SRI# | Structure | MW | Compound Name |
|---|---|---|---|---|
| 1 | 22792 | 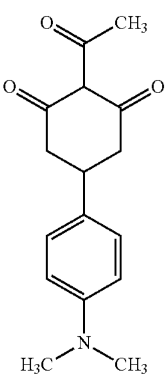 [SMILES: CC(=O)C1C(=O)CC(c2ccc(N(C)C)cc2)CC1=O] | 273.3347 | 1,3-cyclohexanedione, 2-acetyl-5-[4-(N,N-dimethylamino)phenyl]- |
| 2 | 22825 | 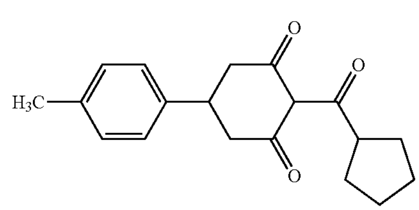 [SMILES: Cc1ccc(C2CC(=O)C(C(=O)C3CCCC3)C(=O)C2)cc1] | 298.3854 | 1,3-cyclohexanedione, 2-cyclopentanecarbonyl-5-[4-methylphenyl]- |

TABLE 1-continued

| Compound No. | SRI# | Structure | MW | Compound Name |
|---|---|---|---|---|
| 3 | 22827 | 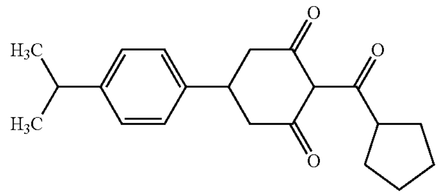 [SMILES: CC(C)c1ccc(C2CC(=O)C(C(=O)C3CCCC3)C(=O)C2)cc1] | 326.4396 | 1,3-cyclohexanedione, 2-cyclopentanecarbonyl-5-[4-(1-methylethyl)phenyl]- |
| 4 | 22830 | 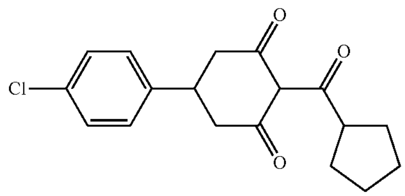 [SMILES: O=C1CC(c2ccc(Cl)cc2)CC(=O)C1C(=O)C1CCCC1] | 318.8033 | 1,3-cyclohexanedione, 2-cyclopentanecarbonyl-5-[4-chlorophenyl]- |
| 5 | 22833 | 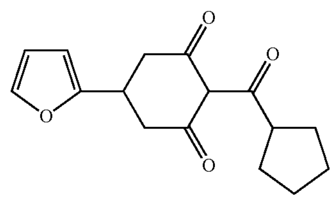 [SMILES: O=C1CC(c2ccco2)CC(=O)C1C(=O)C1CCCC1] | 274.3195 | 1,3-cyclohexanedione, 2-cyclopentanecarbonyl-5-[fur-2-yl]- |
| 6 | 22834 | 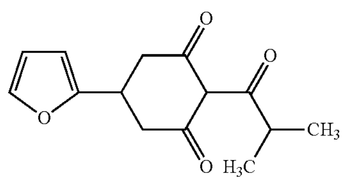 [SMILES: CC(C)C(=O)C1C(=O)CC(c2ccco2)CC1=O] | 248.2812 | 1,3-cyclohexanedione, 2-isobutyryl-5-[fur-2-yl]- |
| 7 | 22838 | 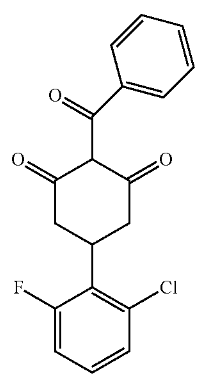 [SMILES: O=C1CC(c2c(F)cccc2Cl)CC(=O)C1C(=O)c1ccccc1] | 344.773 | 1,3-cyclohexanedione, 2-benzoyl-5-[2-chloro-6-fluorophenyl]- |
| 8 | 22841 | 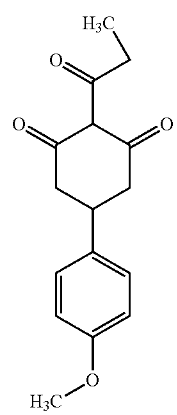 [SMILES: CCC(=O)C1C(=O)CC(c2ccc(OC)cc2)CC1=O] | 274.3195 | 1,3-cyclohexanedione, 2-propanoyl-5-[4-methoxyphenyl]- |

TABLE 1-continued

| Compound No. | SRI# | Structure | MW | Compound Name |
|---|---|---|---|---|
| 9 | 22842 | 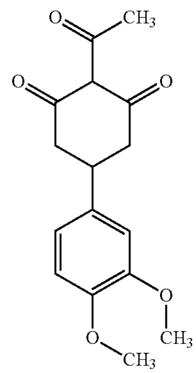 [SMILES: COc1ccc(C2CC(=O)C(C(C)=O)C(=O)C2)cc1OC] | 290.3189 | 1,3-cyclohexanedione, 2-acetyl-5-[3,4-dimethoxyphenyl]- |
| 10 | 22844 | 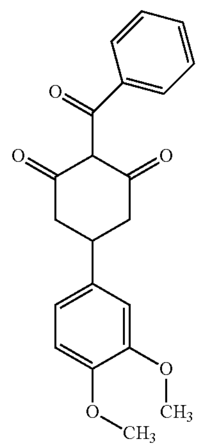 [SMILES: COc1ccc(C2CC(=O)C(C(=O)c3ccccc3)C(=O)C2)cc1OC] | 352.3906 | 1,3-cyclohexanedione, 2-benzoyl-5-[3,4-dimethoxyphenyl]- |
| 11 | 22846 | 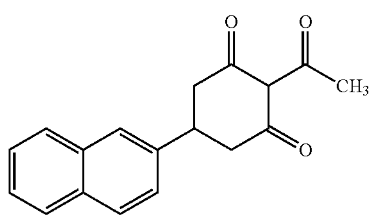 [SMILES: CC(=O)C1C(=O)CC(c2ccc3ccccc3c2)CC1=O] | 280.3264 | 1,3-cyclohexanedione, 2-acetyl-5-[naphth-2-yl]- |
| 12 | 22849 | 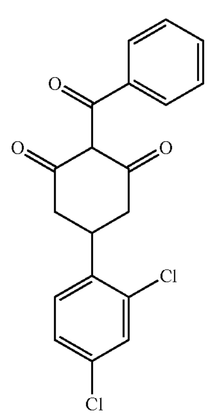 [SMILES: O=C1CC(c2ccc(Cl)cc2Cl)CC(=O)C1C(=O)c1ccccc1] | 361.2276 | 1,3-cyclohexanedione, 2-benzoyl-5-[2,4-dichlorophenyl]- |

TABLE 1-continued

| Compound No. | SRI# | Structure | MW | Compound Name |
|---|---|---|---|---|
| 13 | 22851 | 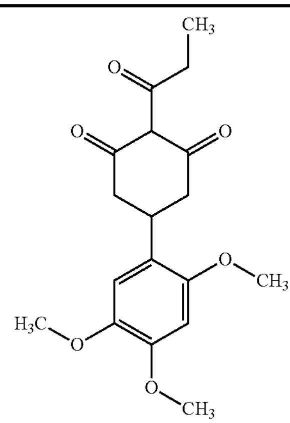 | 334.3724 | 1,3-cyclohexanedione, 2-propanoyl-5-[2,4,5-trimethoxyphenyl]- |
| 14 | 22852 | 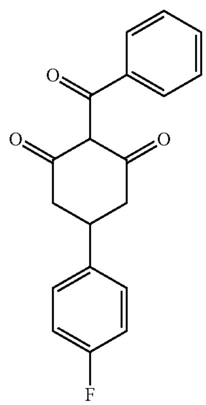 [SMILES: O=C1CC(c2ccc(F)cc2)CC(=O)C1C(=O)c1ccccc1] | 310.328 | 1,3-cyclohexanedione, 2-benzoyl-5-[4-fluorophenyl]- |
| 15 | 22853 | 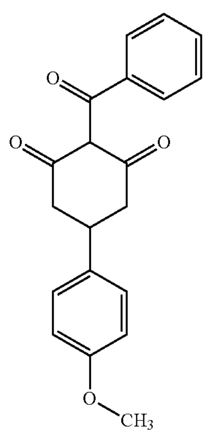 [SMILES: COc1ccc(C2CC(=O)C(C(=O)c3ccccc3)C(=O)C2)cc1] | 322.3641 | 1,3-cyclohexanedione, 2-benzoyl-5-[4-methoxyphenyl]- |
| 16 | 22855 | 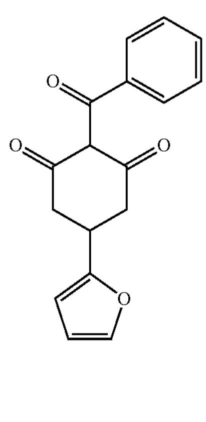 [SMILES: O=C1CC(c2ccco2)CC(=O)C1C(=O)c1ccccc1] | 282.2987 | 1,3-cyclohexanedione, 2-benzoyl-5-[fur-2-yl]- |

TABLE 1-continued

| Compound No. | SRI# | MW | Compound Name |
|---|---|---|---|
| 17 | 22875 | 286.3306 | 1,3-cyclohexanedione, 2-cyclopropanecarbonyl-5-[4-methoxyphenyl]- |
| 18 | 22876 | 314.3848 | 1,3-cyclohexanedione, 2-cyclopentanecarbonyl-5-[4-methoxyphenyl]- |
| 19 | 22877 | 288.3466 | 1,3-cyclohexanedione, 2-isobutyryl-5-[4-methoxyphenyl]- |
| 20 | 22879 | 284.3583 | 1,3-cyclohexanedione, 2-cyclopentanecarbonyl-5-phenyl- |
| 21 | 22881 | 299.373 | 1,3-cyclohexanedione, 2-cyclopropanecarbonyl-5-[4-(N,N-dimethylamino)phenyl]- |
| 22 | 22882 | 327.4272 | 1,3-cyclohexanedione, 2-cyclopentanecarbonyl-5-[4-(N,N-dimethylamino)phenyl]- |
| 23 | 22883 | 301.3889 | 1,3-cyclohexanedione, 2-isobutyrlyl-5-[4-(N,N-dimethylamino)phenyl]- |
| 24 | 22884 | 298.3854 | 1,3-cyclohexanedione, 2-cyclopropanecarbonyl-5-[2,4,6-trimethylphenyl]- |

TABLE 1-continued

| Compound No. | SRI# | Structure | MW | Compound Name |
|---|---|---|---|---|
| 25 | 22885 | 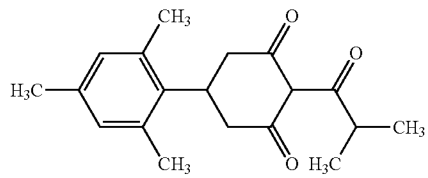 [SMILES: Cc1cc(C)c(C2CC(=O)C(C(=O)C(C)C)C(=O)C2)c(C)c1] | 300.4013 | 1,3-cyclohexanedione, 2-isobutyryl-5-[2,4,6-trimethylphenyl]- |
| 26 | 22886 | 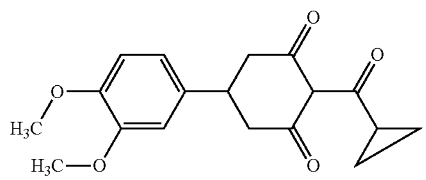 [SMILES: COc1ccc(C2CC(=O)C(C(=O)C3CC3)C(=O)C2)cc1OC] | 316.3571 | 1,3-cyclohexanedione, 2-cyclopropanecarbonyl-5-[3,4-dimethoxyphenyl]- |
| 27 | 22887 | 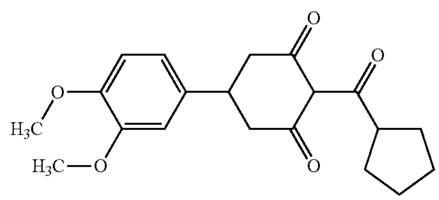 [SMILES: COc1ccc(C2CC(=O)C(C(=O)C3CCCC3)C(=O)C2)cc1OC] | 344.4113 | 1,3-cyclohexanedione, 2-cyclopentanecarbonyl-5-[3,4-dimethoxyphenyl]- |
| 28 | 22888 | 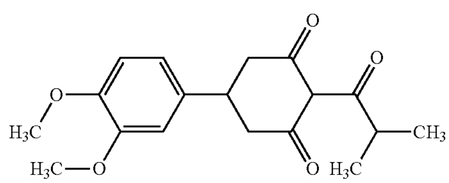 [SMILES: COc1ccc(C2CC(=O)C(C(=O)C(C)C)C(=O)C2)cc1OC] | 318.373 | 1,3-cyclohexanedione, 2-isobutyryl-5-[3,4-dimethoxyphenyl]- |
| 29 | 22891 | 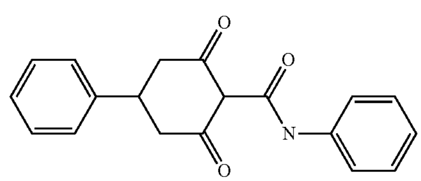 [SMILES: O=C1CC(c2ccccc2)CC(=O)C1C(=O)Nc1ccccc1] | 307.3522 | N,5-diphenylcyclohexane-1,3-dione-2-carboxamide |
| 30 | 22892 | 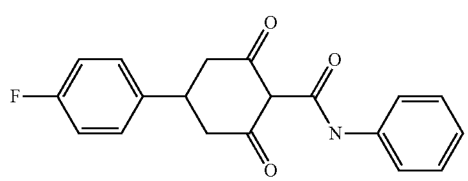 [SMILES: O=C1CC(c2ccc(F)cc2)CC(=O)C1C(=O)Nc1ccccc1] | 325.3427 | N-phenyl-5-[4-fluorophenyl]-cyclohexane-1,3-dione-2-carboxamide |
| 31 | 22893 | 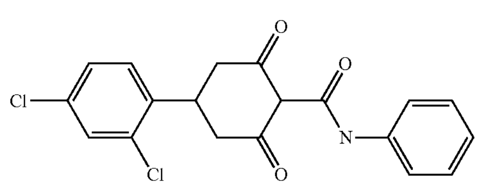 [SMILES: O=C1CC(c2ccc(Cl)cc2Cl)CC(=O)C1C(=O)Nc1ccccc1] | 376.2423 | N-phenyl-5-[2,4-dichlorophenyl]-cyclohexane-1,3-dione-2-carboxamide |
| 32 | 22894 | 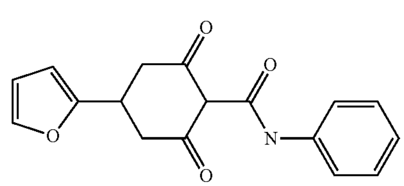 [SMILES: O=C1CC(c2ccco2)CC(=O)C1C(=O)Nc1ccccc1] | 297.3134 | N-phenyl-5-[fur-2-yl]-cyclohexane-1,3-dione-2-carboxamide |

TABLE 1-continued

| Compound No. | SRI# | Structure | MW | Compound Name |
|---|---|---|---|---|
| 33 | 22895 | 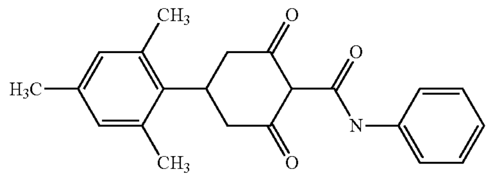 [SMILES: Cc1cc(C)c(C2CC(=O)C(C(=O)Nc3ccccc3)C(=O)C2)c(C)c1] | 349.4335 | N-phenyl-5-[2,4,6-trimethylphenyl]-cyclohexane-1,3-dione-2-carboxamide |
| 34 | 22896 | 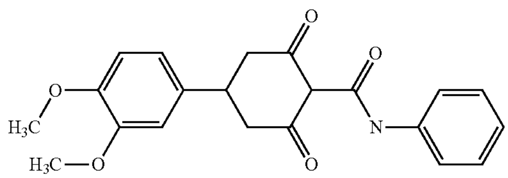 [SMILES: COc1ccc(C2CC(=O)C(C(=O)Nc3ccccc3)C(=O)C2)cc1OC] | 367.4052 | N-phenyl-5-[3,4-dimethoxyphenyl]-cyclohexane-1,3-dione-2-carboxamide |
| 35 | 22899 | 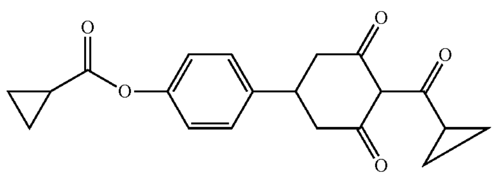 [SMILES: O=C(Oc1ccc(C2CC(=O)C(C(=O)C3CC3)C(=O)C2)cc1)C1CC1] | 340.3794 | 1,3-cyclohexanedione, 2-cyclopropanecarbonyl-5-[4-(cyclopropanecarboxy)phenyl]- |
| 36 | 22928 | 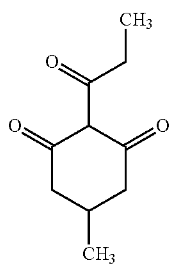 | 182.2213 | 1,3-cyclohexanedione, 2-propanoyl-5-methyl- |
| 37 | 22929 | 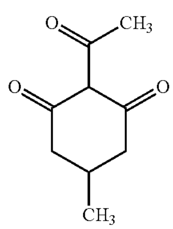 | 168.1942 | 1,3-cyclohexanedione, 2-acetyl-5-methyl- |
| 38 | 22938 | 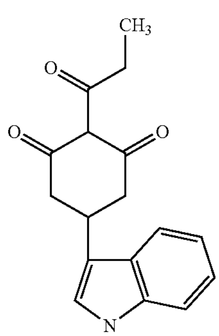 [SMILES: CCC(=O)C1C(=O)CC(c2c[nH]c3ccccc23)CC1=O] | 283.3299 | 1,3-cyclohexanedione, 2-propanoyl-5-[indol-3-yl]- |

TABLE 1-continued
| Compound No. | SRI# | Structure | MW | Compound Name |
|---|---|---|---|---|
| 39 | 22940 | 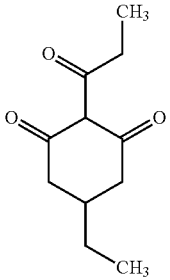 | 196.2484 | 1,3-cyclohexanedione, 2-propanoyl-5-ethyl- |
| 40 | 22946 | 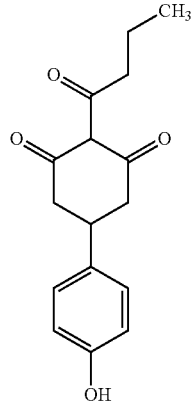 [SMILES: CCCC(=O)C1C(=O)CC(c2ccc(O)cc2)CC1=O] | 274.3195 | 1,3-cyclohexanedione, 2-butyryl-5-[4-hydroxyphenyl]- |
| 41 | 22788 | 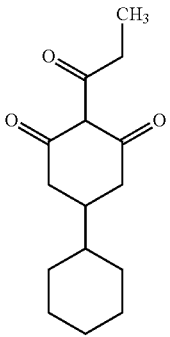 | 250.3408 | 1,3-cyclohexanedione, 2-propanoyl-5-cyclohexyl- |
| 42 | 22789 | 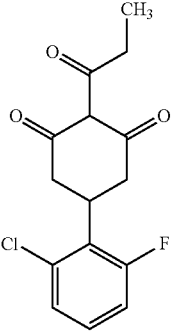 [SMILES: CCC(=O)C1C(=O)CC(c2c(F)cccc2Cl)CC1=O] | 296.7284 | 1,3-cyclohexanedione, 2-propanoyl-5-[2-chloro-6-fluorophenyl]- |

TABLE 1-continued

| Compound No. | SRI# | Structure | MW | Compound Name |
|---|---|---|---|---|
| 43 | 22790 | 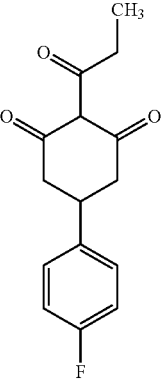 | 262.2834 | 1,3-cyclohexanedione, 2-propanoyl-5-[4-fluorophenyl]- |
| 44 | 22791 | 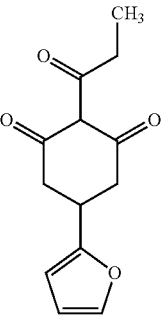 | 234.2541 | 1,3-cyclohexanedione, 2-propanoyl-5-[fur-2-yl]- |
| 45 | 22821 | 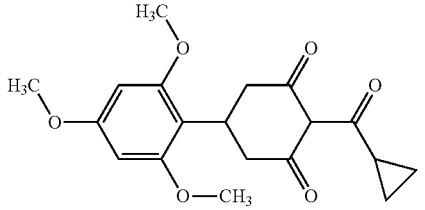 [SMILES: COc1cc(OC)c(C2CC(=O)C(C(=O)C3CC3)C(=O)C2)c(OC)c1] | 346.3836 | 1,3-cyclohexanedione, 2-cyclopropanecarbonyl-5-[2,4,6-trimethoxyphenyl]- |
| 46 | 22822 | 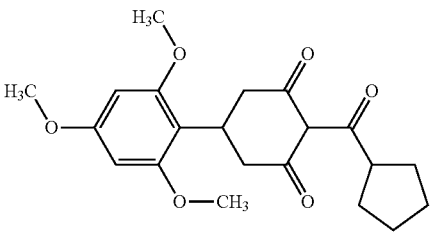 [SMILES: COc1cc(OC)c(C2CC(=O)C(C(=O)C3CCCC3)C(=O)C2)c(OC)c1] | 374.4378 | 1,3-cyclohexanedione, 2-cyclopentanecarbonyl-5-[2,4,6-trimethoxyphenyl]- |
| 47 | 22823 | 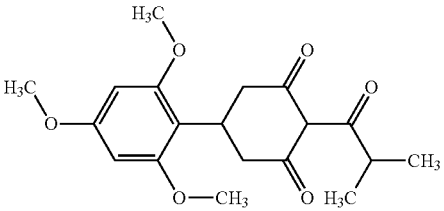 [SMILES: COc1cc(OC)c(C2CC(=O)C(C(=O)C(C)C)C(=O)C2)c(OC)c1] | 348.3995 | 1,3-cyclohexanedione, 2-isobutyryl-5-[2,4,6-trimethoxyphenyl]- |
| 48 | 22824 | 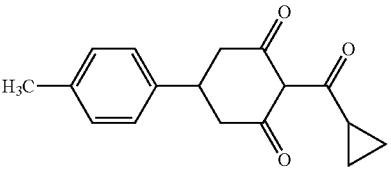 [SMILES: Cc1ccc(C2CC(=O)C(C(=O)C3CC3)C(=O)C2)cc1] | 270.3312 | 1,3-cyclohexanedione, 2-cyclopropanecarbonyl-5-[4-methylphenyl]- |

TABLE 1-continued

| Compound No. | SRI# | Structure | MW | Compound Name |
|---|---|---|---|---|
| 49 | 22826 | 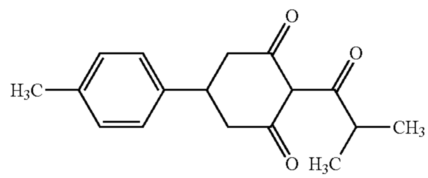 [SMILES: Cc1ccc(C2CC(=O)C(C(=O)C(C)C)C(=O)C2)cc1] | 272.3472 | 1,3-cyclohexanedione, 2-isobutyryl-5-[4-methylphenyl]- |
| 50 | 22828 | 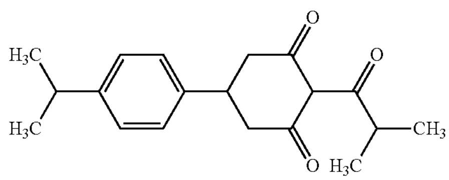 [SMILES: CC(C)C(=O)C1C(=O)CC(c2ccc(C(C)C)cc2)CC1=O] | 300.4013 | 1,3-cyclohexanedione, 2-isobutyryl-5-[4-(1-methylethyl)phenyl]- |
| 51 | 22829 | 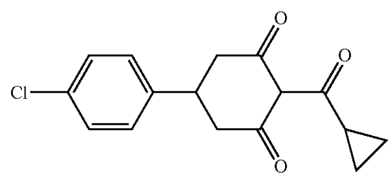 [SMILES: O=C1CC(c2ccc(Cl)cc2)CC(=O)C1C(=O)C1CC1] | 290.7492 | 1,3-cyclohexanedione, 2-cyclopropanecarbonyl-5-[4-chlorophenyl]- |
| 52 | 22831 | 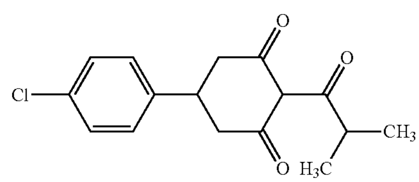 [SMILES: CC(C)C(=O)C1C(=O)CC(c2ccc(Cl)cc2)CC1=O] | 292.7651 | 1,3-cyclohexanedione, 2-isobutyryl-5-[4-chlorophenyl]- |
| 53 | 22832 | 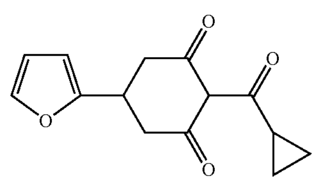 [SMILES: O=C1CC(c2ccco2)CC(=O)C1C(=O)C1CC1] | 246.2653 | 1,3-cyclohexanedione, 2-cyclopropanecarbonyl-5-[fur-2-yl]- |
| 54 | 22835 | 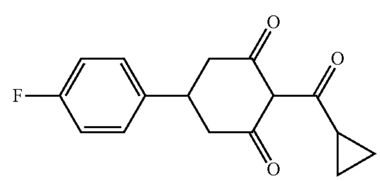 [SMILES: O=C1CC(c2ccc(F)cc2)CC(=O)C1C(=O)C1CC1] | 274.2946 | 1,3-cyclohexanedione, 2-cyclopropanecarbonyl-5-[4-fluorophenyl]- |
| 55 | 22836 | 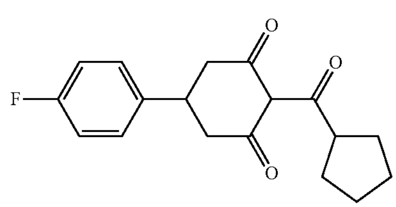 [SMILES: O=C1CC(c2ccc(F)cc2)CC(=O)C1C(=O)C1CCCC1] | 302.3487 | 1,3-cyclohexanedione, 2-cyclopentanecarbonyl-5-[4-fluorophenyl]- |
| 56 | 22837 | 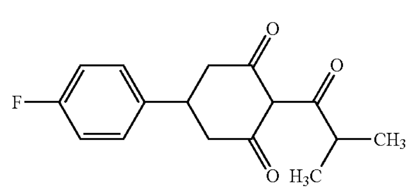 [SMILES: CC(C)C(=O)C1C(=O)CC(c2ccc(F)cc2)CC1=O] | 276.3105 | 1,3-cyclohexanedione, 2-isobutyryl-5-[4-fluorophenyl]- |

TABLE 1-continued

| Compound No. | SRI# | Structure | MW | Compound Name |
|---|---|---|---|---|
| 57 | 22839 | 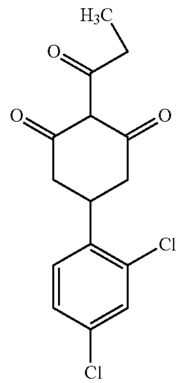 [SMILES: CCC(=O)C1C(=O)CC(c2ccc(Cl)cc2Cl)CC1=O] | 313.183 | 1,3-cyclohexanedione, 2-propanoyl-5-[2,4-dichlorophenyl]- |
| 58 | 22840 | 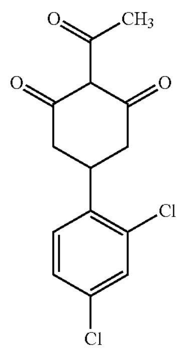 [SMILES: CC(=O)C1C(=O)CC(c2ccc(Cl)cc2Cl)CC1=O] | 299.1559 | 1,3-cyclohexanedione, 2-acetyl-5-[2,4-dichlorophenyl]- |
| 59 | 22843 | 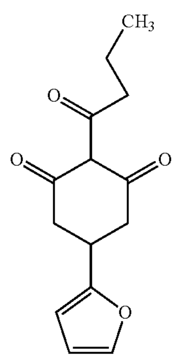 [SMILES: CCCC(=O)C1C(=O)CC(c2ccco2)CC1=O] | 248.2812 | 1,3-cyclohexanedione, 2-butyryl-5-[fur-2-yl]- |
| 60 | 22845 | 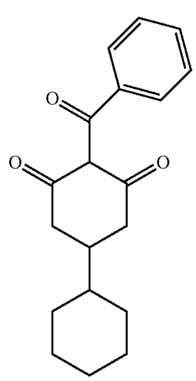 [SMILES: O=C1CC(C2CCCCC2)CC(=O)C1C(=O)c1ccccc1] | 298.3854 | 1,3-cyclohexanedione, 2-benzoyl-5-cyclohexyl- |

TABLE 1-continued

| Compound No. | SRI# | Structure | MW | Compound Name |
|---|---|---|---|---|
| 61 | 22847 | 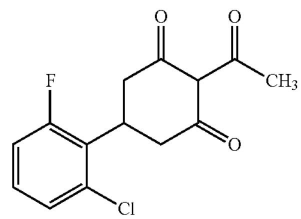 [SMILES: CC(=O)C1C(=O)CC(c2c(F)cccc2Cl)CC1=O] | 282.7013 | 1,3-cyclohexanedione, 2-acetyl-5-[2-chloro-6-fluorophenyl]- |
| 62 | 22848 | 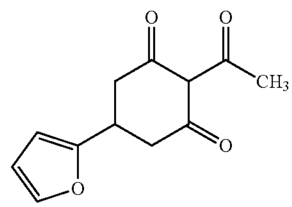 [SMILES: CC(=O)C1C(=O)CC(c2ccco2)CC1=O] | 220.227 | 1,3-cyclohexanedione, 2-acetyl-5-[fur-2-yl]- |
| 63 | 22850 | 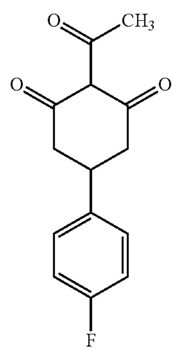 [SMILES: CC(=O)C1C(=O)CC(c2ccc(F)cc2)CC1=O] | 248.2563 | 1,3-cyclohexanedione, 2-acetyl-5-[4-fluorophenyl]- |
| 64 | 22854 | 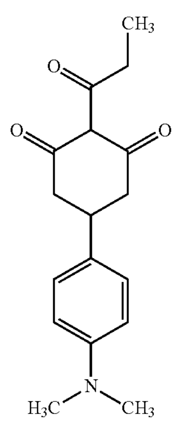 [SMILES: CCC(=O)C1C(=O)CC(c2ccc(N(C)C)cc2)CC1=O] | 287.3618 | 1,3-cyclohexanedione, 2-propanoyl-5-[4(N,N-dimethylamino)phenyl]- |
| 65 | 22856 | 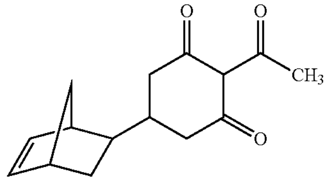 [SMILES: CC(=O)C1C(=O)CC(C2CC3C=CC2C3)CC1=O] | 246.3089 | 1,3-cyclohexanedione, 2-acetyl-5-[bicyclo[2.2.1]hept-2-en-5-yl]- |

TABLE 1-continued

| Compound No. | SRI# | Structure | MW | Compound Name |
|---|---|---|---|---|
| 66 | 22857 | 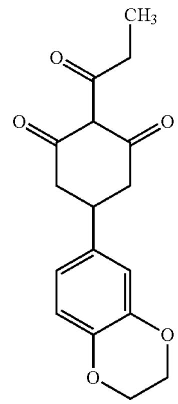 [SMILES: CCC(=O)C1C(=O)CC(c2ccc3c(c2)OCCO3)CC1=O] | 302.33 | 1,3-cyclohexanedione, 2-propanoyl-5-[(3,4-ethylenedioxy)phenyl]- |
| 67 | 22878 | 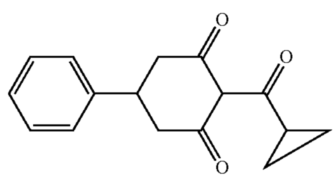 [SMILES: O=C1CC(c2ccccc2)CC(=O)C1C(=O)C1CC1] | 256.3041 | 1,3-cyclohexanedione, 2-cyclopropanecarbonyl-5-phenyl- |
| 68 | 22880 | 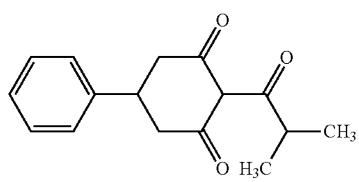 [SMILES: CC(C)C(=O)C1C(=O)CC(c2ccccc2)CC1=O] | 258.3201 | 1,3-cyclohexanedione, 2-isobutyryl-5-phenyl- |
| 69 | 22889 | 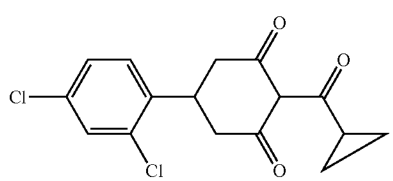 [SMILES: O=C1CC(c2ccc(Cl)cc2Cl)CC(=O)C1C(=O)C1CC1] | 325.1942 | 1,3-cyclohexanedione, 2-cyclopropanecarbonyl-5-[2,4-dichlorophenyl]- |
| 70 | 22890 | 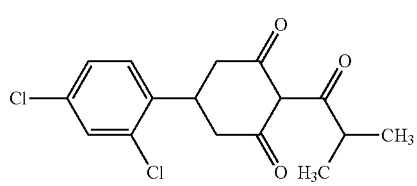 [SMILES: CC(C)C(=O)C1C(=O)CC(c2ccc(Cl)cc2Cl)CC1=O] | 327.2101 | 1,3-cyclohexanedione, 2-isobutyryl-5-[2,4-dichlorophenyl]- |
| 71 | 22897 | 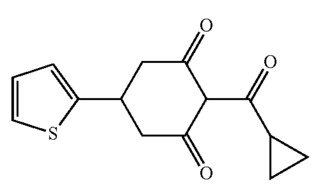 [SMILES: O=C1CC(c2cccs2)CC(=O)C1C(=O)C1CC1] | 262.3299 | 1,3-cyclohexanedione, 2-cyclopropanecarbonyl-5-[thien-2-yl]- |
| 72 | 22898 | 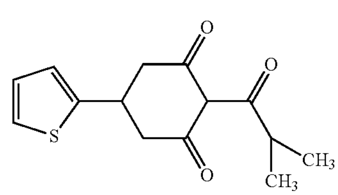 [SMILES: CC(C)C(=O)C1C(=O)CC(c2cccs2)CC1=O] | 264.3458 | 1,3-cyclohexanedione, 2-isobutyryl-5-[thien-2-yl]- |

TABLE 1-continued
| Compound No. | SRI# | Structure | MW | Compound Name |
|---|---|---|---|---|
| 73 | 22926 | 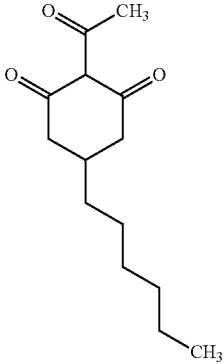 [SMILES: CCCCCCC1CC(=O)C(C(C)=O)C(=O)C1] | 238.3296 | 1,3-cyclohexanedione, 2-acetyl-5-hexyl- |
| 74 | 22927 | 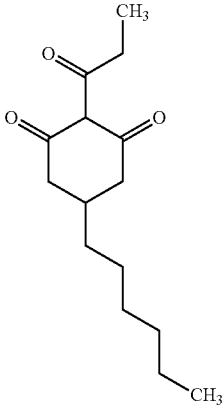 [SMILES: CCCCCCC1CC(=O)C(C(=O)CC)C(=O)C1] | 252.3567 | 1,3-cyclohexanedione, 2-propanoyl-5-hexyl- |
| 75 | 22930 | 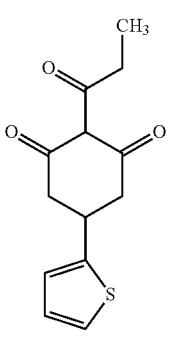 [SMILES: CCC(=O)C1C(=O)CC(c2cccs2)CC1=O] | 250.3187 | 1,3-cyclohexanedione, 2-propanoyl-5-[thien-2-yl]- |
| 76 | 22931 | 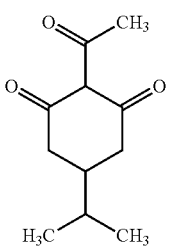 | 196.2484 | 1,3-cyclohexanedione, 2-acetyl-5-(1-methylethyl)- |

TABLE 1-continued

| Compound No. | SRI# | Structure | MW | Compound Name |
|---|---|---|---|---|
| 77 | 22932 | 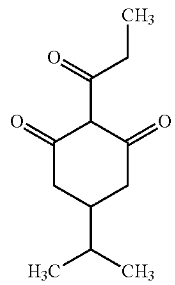 | 210.2755 | 1,3-cyclohexanedione, 2-propanoyl-5-(1-methylethyl)- |
| 78 | 22933 | 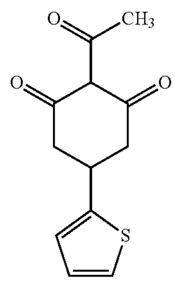 [SMILES: CC(=O)C1C(=O)CC(c2cccs2)CC1=O] | 236.2916 | 1,3-cyclohexanedione, 2-acetyl-5-[thien-2-yl]- |
| 79 | 22934 | 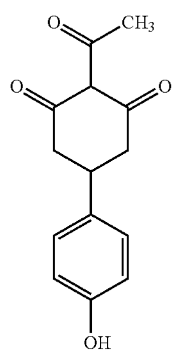 [SMILES: CC(=O)C1C(=O)CC(c2ccc(O)cc2)CC1=O] | 246.2653 | 1,3-cyclohexanedione, 2-acetyl-5-[4-hydroxyphenyl]- |
| 80 | 22935 | 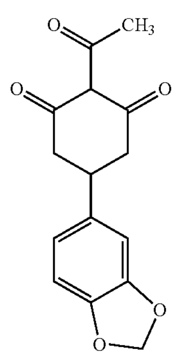 [SMILES: CC(=O)C1C(=O)CC(c2ccc3c(c2)OCO3)CC1=O] | 274.2758 | 1,3-cyclohexanedione, 2-acetyl-5-[3,4-methylenedioxyphenyl]- |

TABLE 1-continued

| Compound No. | SRI# | Structure | MW | Compound Name |
|---|---|---|---|---|
| 81 | 22936 | 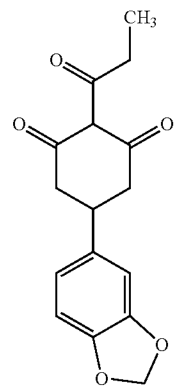 [SMILES: CCC(=O)C1C(=O)CC(c2ccc3c(c2)OCO3)CC1=O] | 288.3029 | 1,3-cyclohexanedione, 2-propanoyl-5-[3,4-methylenedioxyphenyl]- |
| 82 | 22937 | 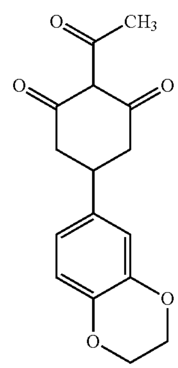 [SMILES: CC(=O)C1C(=O)CC(c2ccc3c(c2)OCCO3)CC1=O] | 288.3029 | 1,3-cyclohexanedione, 2-acetyl-5-[3,4-ethylenedioxyphenyl]- |
| 83 | 22939 | 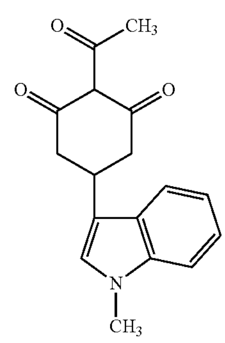 [SMILES: CC(=O)C1C(=O)CC(c2cn(C)c3ccccc23)CC1=O] | 283.3299 | 1,3-cyclohexanedione, 2-acetyl-5-[N-methylindol-3-yl]- |
| 84 | 22941 | 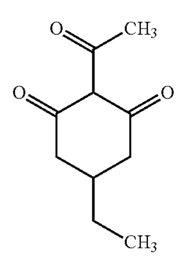 | 182.2213 | 1,3-cyclohexanedione, 2-acetyl-5-ethyl- |

TABLE 1-continued
| Compound No. | SRI# | Structure | MW | Compound Name |
|---|---|---|---|---|
| 85 | 22942 | 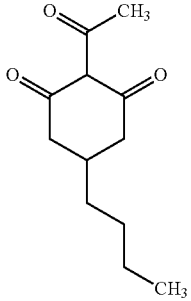 | 210.2755 | 1,3-cyclohexanedione, 2-acetyl-5-butyl- |
| 86 | 22943 | 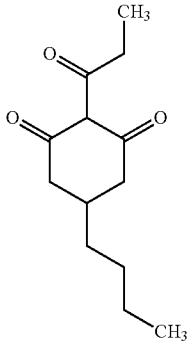 [SMILES: CCCCC1CC(=O)C(C(=O)CC)C(=O)C1] | 224.3026 | 1,3-cyclohexanedione, 2-propanoyl-5-butyl- |
| 87 | 22944 | 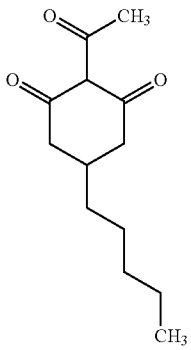 [SMILES: CCCCCC1CC(=O)C(C(C)=O)C(=O)C1] | 224.3026 | 1,3-cyclohexanedione, 2-acetyl-5-pentyl- |
| 88 | 22945 | 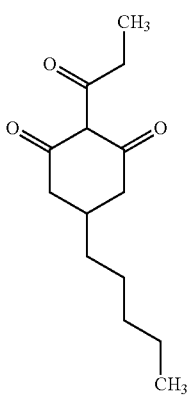 [SMILES: CCCCCC1CC(=O)C(C(=O)CC)C(=O)C1] | 238.3296 | 1,3-cyclohexanedione, 2-propanoyl-5-pentyl- |

TABLE 1-continued

| Compound No. | SRI# | Structure | MW | Compound Name |
|---|---|---|---|---|
| 89 | 22947 | (structure) | 311.3841 | 1,3-cyclohexanedione, 2-butyryl-5-[N-methylindol-3-yl]- |
| 90 | 22965 | (structure) | 260.336 | 1,3-cyclohexanedione, 2-propanoyl-5-[bicyclo[2.2.1]hept-2-en-5-yl]- |

EXAMPLE 4

DeaD assay results for selected compounds of the present invention are listed in the following table:

TABLE 2

| | SRI# or ID | | average improvement, 250 nM to 1μM | # of measurements | average improvement, 125 nM | # of measurements | average improvement, 0.5 to 100 nM | # of measurements |
|---|---|---|---|---|---|---|---|---|
| | 22790 | C1-2 | 2.64 | 8 | 2.85 | 3 | 1.37 | 14 |
| | 22788 | C1-1 | 2.74 | 7 | 3.40 | 3 | 1.75 | 13 |
| | 22789 | | 2.62 | 6 | 2.61 | 3 | 1.30 | 8 |
| | 22965 | C1-5 | 2.57 | 6 | 3.65 | 1 | 1.72 | 14 |
| | 22945 | | 2.54 | 2 | 1.96 | 1 | ND | 0 |
| | 22942 | C1-4 | 2.49 | 5 | 2.87 | 1 | 1.71 | 6 |
| | 22933 | C1-3 | 2.55 | 5 | 2.71 | 1 | 1.70 | 6 |
| | 22930 | | 2.33 | 3 | 2.21 | 1 | ND | 0 |
| | 22943 | | 2.33 | 3 | 2.79 | 1 | ND | 0 |
| | 22944 | | 2.28 | 3 | 2.72 | 1 | 1.21 | 8 |
| | 22835 | | 2.21 | 5 | 2.48 | 2 | ND | 0 |
| | 22856 | | 2.18 | 3 | 3.18 | 1 | ND | 0 |
| | 22847 | | 2.17 | 3 | 3.25 | 1 | ND | 0 |
| | 22791 | | 2.15 | 3 | 1.77 | 2 | ND | 0 |
| | 22845 | | 2.11 | 5 | 1.99 | 2 | ND | 0 |
| | 22878 | | 2.11 | 5 | 2.62 | 2 | ND | 0 |
| | 22931 | | 2.09 | 3 | 1.86 | 1 | ND | 0 |
| control | S3-5 | S3-5 | 1.91 | 11 | 1.81 | 3 | 1.00 | 8 |
| | 22926 | | 1.87 | 3 | 0.99 | 1 | ND | 0 |
| | 22840 | | 1.87 | 3 | 2.24 | 1 | ND | 0 |
| | 22897 | | 1.85 | 5 | 1.25 | 1 | ND | 0 |
| | 22932 | | 1.80 | 3 | 1.76 | 1 | ND | 0 |
| | 22837 | | 1.72 | 3 | ND | 0 | ND | 0 |
| | 22947 | | 1.64 | 3 | ND | 0 | ND | 0 |
| | 22889 | | 1.64 | 3 | ND | 0 | ND | 0 |
| | 22821 | | 1.62 | 3 | 1.27 | 2 | ND | 0 |
| | 22941 | | 1.62 | 3 | ND | 0 | ND | 0 |
| | 22939 | | 1.60 | 3 | ND | 0 | ND | 0 |
| | 22850 | | 1.59 | 3 | ND | 0 | ND | 0 |
| | 22880 | | 1.59 | 5 | 1.49 | 1 | ND | 0 |
| | 22848 | | 1.58 | 3 | ND | 0 | ND | 0 |

TABLE 2-continued

| | SRI# or ID | | average improvement, 250 nM to 1μM | # of measurements | average improvement, 125 nM | # of measurements | average improvement, 0.5 to 100 nM | # of measurements |
|---|---|---|---|---|---|---|---|---|
| control | #3-11 | #3-11 | 1.30 | 9 | ND | 0 | ND | 0 |
| | 22935 | | 1.51 | 3 | ND | 0 | ND | 0 |
| | 22890 | | 1.46 | 3 | ND | 0 | ND | 0 |
| | 22936 | | 1.46 | 3 | ND | 0 | ND | 0 |
| | 22927 | | 1.43 | 3 | ND | 0 | ND | 0 |
| | 22824 | | 1.42 | 3 | 1.32 | 1 | ND | 0 |
| | 22898 | | 1.37 | 3 | ND | 0 | ND | 0 |

EXAMPLE V

This Example demonstrates the effects of the compounds on inflammatory responses in vitro and in an animal model of inflammation.

Figure 3:
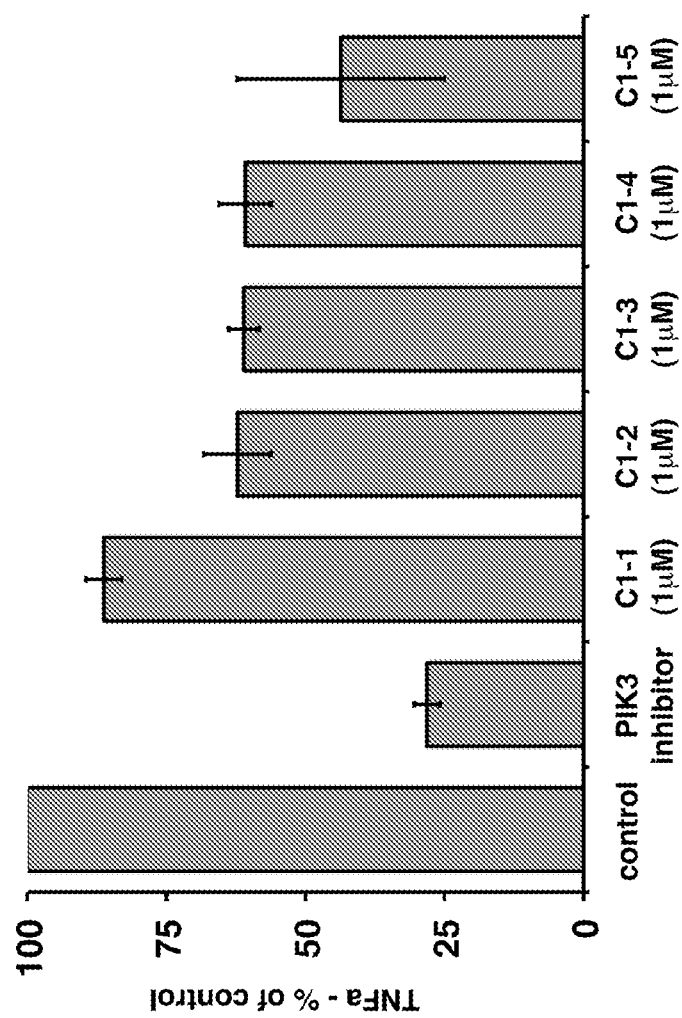
FIG. 3. Graphical results demonstrating a reduction in in vitro anti-inflammatory activity in RAW 264.7 cells (marine leukemic monocot macrophage cell line) by using compounds provided by the invention. To obtain the data summarized in FIG. 3, RAW 246.7 cells were incubated with Scrims (compounds of present invention) (1 uM), PI3K inhibitor positive control (LY-294002; 25 uM) or vehicle (DMSO) for 1 hr. LPS (10 ng/ml) was added to the medium. 6 hrs post LPS administration medium was collected and analyzed for TNFa levels using ELISA.

In vitro anti-inflammatory activity in RAW 264.7 cells (murine leukaemic monocyte macrophage cell line): Lipopolysaccharide (LPS)-induced secretion of cytokines from RAW cells is a recognized in vitro assay for anti-inflammatory drugs. The anti-inflammatory activities of C1-1, C1-2, C1-3, C1-4, and C1-5 in the RAW cell model. RAW cells exposed to LPS were incubated with each of the five molecules at 1 micromolar concentration. The PIK3 inhibitor LY-294002 was used at 25 micromolar as a positive control. As shown in FIG. 3 all five C1-SCRINs exhibited anti-inflammatory activity as assessed by a reduction relative to vehicle treated cells of secreted Tumor Necrosis Factor-alpha (TNF-α). LPS was administered at 10 ng/ml for 6-hrs. TNF-α levels were quantified by ELISA assay. Results are presented as % of control with standard deviations of three replicates.

Figure 4:
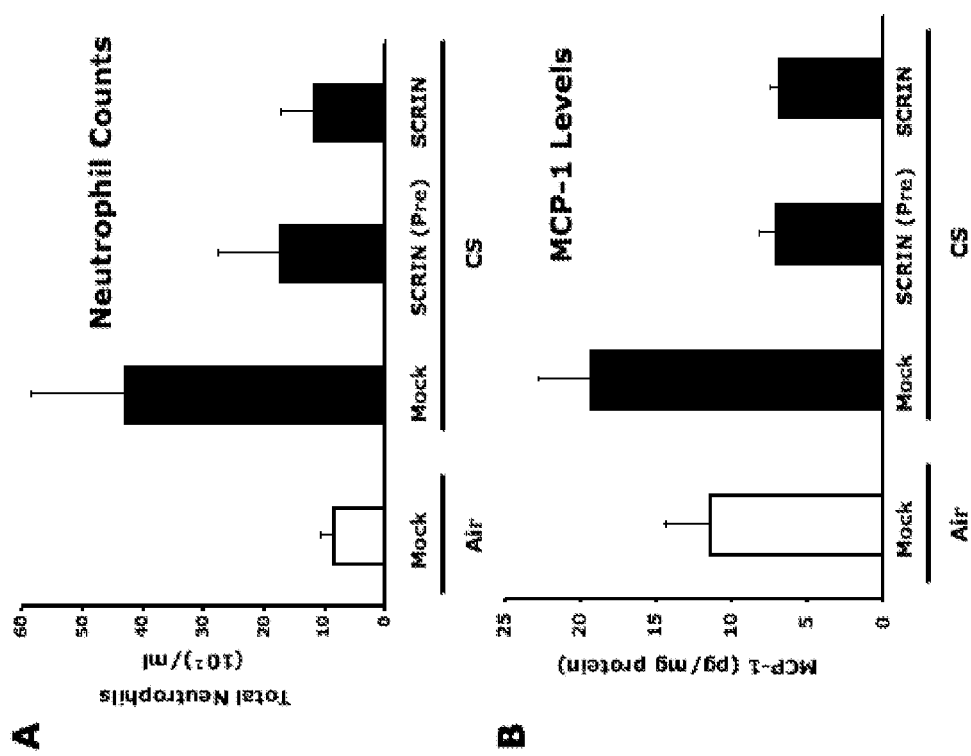
FIG. 4. Graphical results demonstrating in vivo inhibition of cigarette smoke-induced inflammation of mouse lungs. To obtain the data summarized in FIG. 4, Mice were exposed to cigarette smoke or filtered air for 3 consecutive days. They were treated ip with vehicle or Cob 1-2 (5 mg/kg) in DMSO: 1 group was treated daily during smoke exposure period and 1 group was pre-treated with 2 doses per week during the week prior to the smoke exposure and daily during the smoke exposure. On day 4, mice were sacrificed. Their lungs were washed and BAL fluid was stained for Europhiles count. The lungs were homogenized for ELISA quantifying MCP-1 levels.

In vivo prevention of cigarette smoke-induced inflammation of mouse lungs: Exposing mice to cigarette smoke induces an acute inflammatory response in the lungs. Cigarette smoke-induced inflammation in the lungs was assessed by quantifying the ratio of macrophages to Europhiles in bronchoalveolar lavage fluid (BALF), and levels of pro-inflammatory markers such as MCP-1 in lung tissue (Yao H, Edirisinghe I, Rajendrasozhan S, Yang S R, Caito S, Adenuga D, Rahman I. Cigarette smoke-mediated inflammatory and oxidative responses are strain-dependent in mice. Am. J. Physiol Lung Cell Mol Physiol 2008; 294: L1174-L1186.). C1-2 significantly reduced the inflammatory response in the lungs of mice exposed to cigarette smoke. As shown in FIG. 4A, C1-2 treatment lowered total Europhiles count to near background levels observed in air-exposed control mice. Pre-treatment with C1-2 for two weeks prior to smoke exposure did not change the beneficial affect of C1-2 when administered one day prior to, and during, the period of smoke exposure. As shown in FIG. 4B, levels of the chemokine MCP-1 were decreased in a statistically significant fashion in the lungs of treated mice to the normal levels as measured in air-exposed mice.

Figure 5:
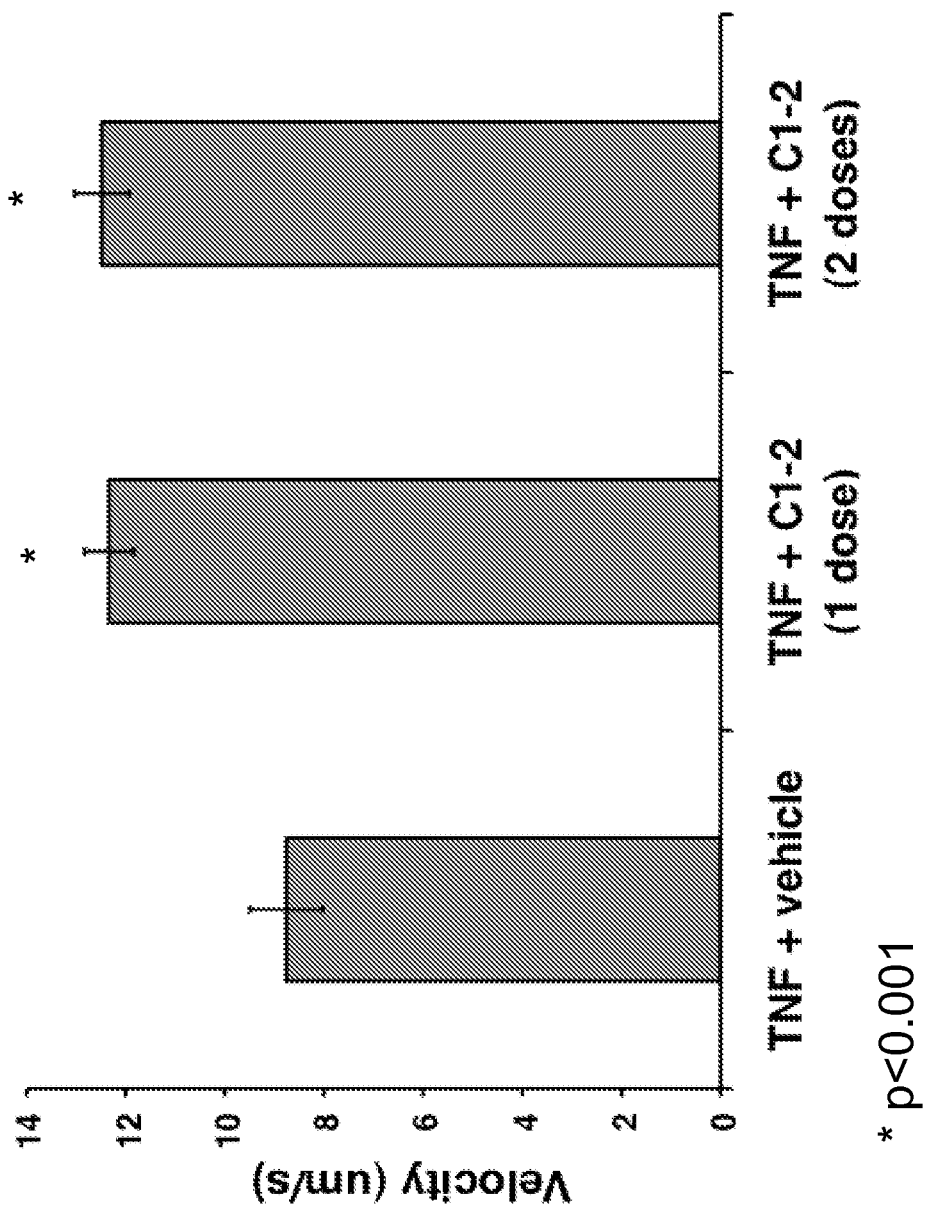
FIG. 5. Graphical results showing in vivo reduction of TNF-α-induced vascular inflammation in mice. To obtain the data summarized in FIG. 5, mice (3 each group) were injected with vehicle or Cob 1-2 (ip, 6 mg/kg in DMSO). Two treatments were used: i) 1 dose an hour before TNFa and, ii) 2 doses (24 hrs and 1 hr before TNFa). TNFa was administered ip (20 ug/kg). 3 hours post TNFa administration, mice were anesthetized, their mesentery was exposed and placed on an inverted fluorescent microscope stage. Lymphocyte velocities within veins was determined by analyzing video recordings

In vivo reduction of TNF-α-induced vascular inflammation in mice: The affects of drugs on vascular inflammation can be assessed by quantifying the rates of leukocytes rolling in mouse mesenteric vessels following intraperitoneal administration of TNF-α (Craig N. Morrell, Kenji Matsushita, and Charles J. Lowenstein. A Novel Inhibitor of N-Ethylmaleimide-Sensitive Factor Decreases Leukocyte Trafficking and Peritonitis. JPET 2005; 314:155-161). Vascular inflammation was induced in two groups of mice that were treated with C1-2 either once (1 hour) or twice (24 hours and 1 hour) prior to TNF-α administration. As shown in FIG. 5, C1-2 significantly increased leukocytes velocity when compared to TNF-α-treated control mice.

While the invention has been particularly shown and described with reference to specific embodiments (some of which are preferred embodiments), it should be understood by those having skill in the art that various changes in form and detail may be made therein without departing from the spirit and scope of the present invention as disclosed herein.

What is claimed is:

1. A pharmaceutical composition comprising a compound with the following structure:

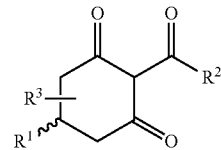

wherein $R^1$ and $R^2$ are independently
an aliphatic alkyl group having 1 carbon to 8 carbons, wherein the aliphatic alkyl group is branched, saturated or has one or more carbon-carbon multiple bonds, and is, optionally, substituted with one or more halogens,
a cyclic alkyl group having 3 carbons to 8 carbons, wherein the cyclic alkyl group is saturated or has one or more carbon-carbon multiple bonds, and is, optionally, substituted with one or more alkyl groups having 1 carbon to 6 carbons,
an aryl group, wherein the aryl group has a single, multiple-ring or fused-ring structure, and each ring is, optionally, independently substituted with one or more groups selected from halogen, hydroxy, alkoxy group having 1 carbon to 6 carbons (wherein if the compound is substituted with two adjacent alkoxy groups the groups are, optionally, linked by an alkyl group having 1 carbon to 4 carbons), amino group, alkylamino group having one alkyl group or two alkyl groups, wherein each alkyl group has 1 carbon to 6 carbons, arylamino group having one aromatic group or two aromatic groups, wherein each aryl group has 4 carbons to 6 carbons, alkyloxy group, wherein the alkyl group has 1 carbon to 6 carbons and is linear, branched or cyclic, and aryloxy group, wherein the aryl group has 4 carbons to 6 carbons,
an aralkyl group, wherein the araalkyl group is attached via the aliphatic moiety having 1 carbon to 8 carbons and an aromatic moiety having 4 carbons to 8 carbons, or
a heterocyclic group having 3 carbons to 8 carbons, wherein the heterocyclic group is saturated or comprises one or more carbon-carbon multiple bonds, and
$R^3$ is an optional substitution and is any of the $R^1$ and $R^2$ groups.

2. The pharmaceutical composition of claim 1, wherein the compound has the structure:

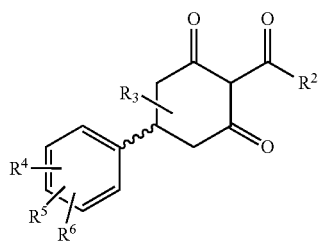

wherein the compound has at least one of $R^4$, $R^5$ and $R^6$, and $R^4$, $R^5$ and $R^6$ are independently selected from halogen, hydroxy, alkoxy group having 1 carbon to 6 carbons, wherein if the compound is substituted with two adjacent alkoxy groups the groups are, optionally, linked by an alkyl group having from 1 carbon to 4 carbons, amino group, alkylamino group having one or two alkyl groups, wherein each alkyl group has 1 carbon to 6 carbons, alkyloxy group, wherein the alkyl group has 1 carbon to 6 carbons and is linear, branched or cyclic, and aryloxy group, wherein the alkyl group has 4 carbons to 6 carbons.

3. The pharmaceutical composition of claim 2, wherein the compound has one of the structures:

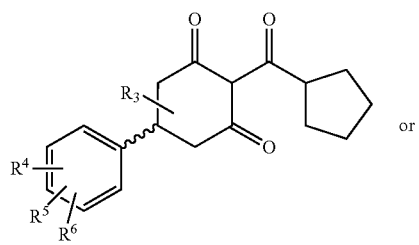 or

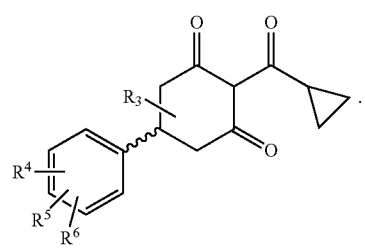

4. The pharmaceutical composition of claim 1, wherein the compound has the following structure:

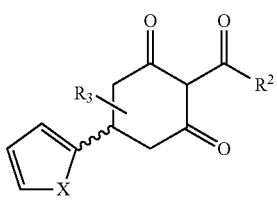

wherein X is O, N, or S.

5. The pharmaceutical composition of claim 4, wherein the compound has one of the following structures:

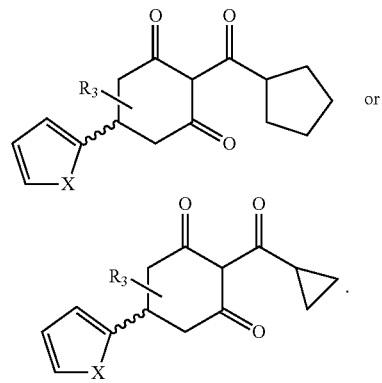

6. The pharmaceutical composition of claim 1, wherein the compound has the following structure:

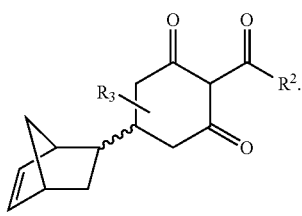

7. The pharmaceutical composition of claim 1, wherein the compound has the following structure:

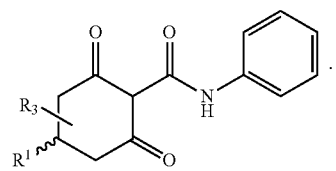

8. The pharmaceutical composition of claim 7, wherein the compound has one of the following structures:

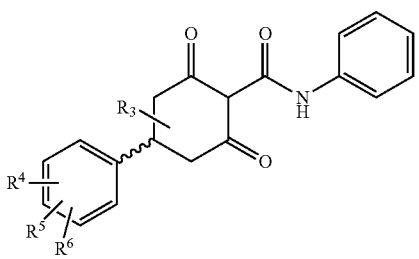

wherein the compound has at least one of $R^4$, $R^5$ and $R^6$, and $R^4$, $R^5$ and $R^6$
are independently selected from halogen, hydroxy, alkoxy group having 1 carbon to 6 carbons, wherein if the compound is substituted with two adjacent alkoxy groups the groups are, optionally, linked by an alkyl group having from 1 carbon to 4 carbons, amino group, alkylamino group having one or two alkyl groups, wherein each alkyl group comprises 1 carbon to 6 carbons, alkyloxy group, wherein the alkyl group comprises 1 carbon to 6 carbons and is linear, branched or cyclic, and aryloxy group, wherein the alkyl group comprises 4 carbons to 6 carbons, or

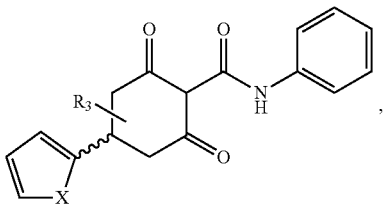

, wherein X is O, N or S.

9. The pharmaceutical composition of claim 1, wherein the compound has one of the following structures:

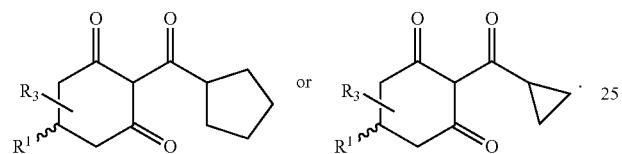

10. The pharmaceutical composition of claim 1, where the compound is selected from:

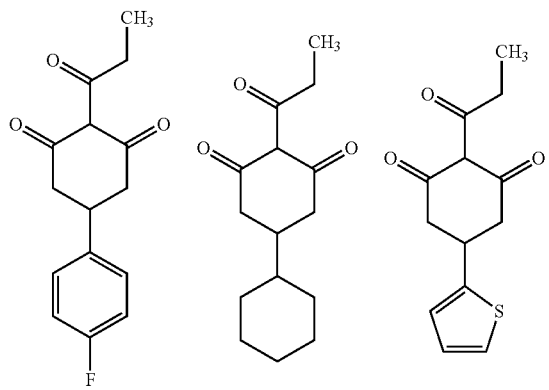

and

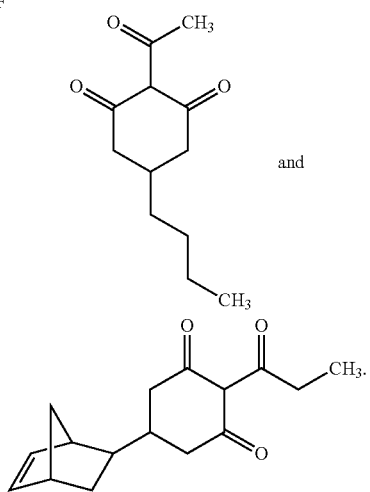

11. A method for reducing of inflammation in an individual comprising administering a composition of claim 1 to the individual, whereby inflammation in the individual organism is reduced subsequent to the administration.

12. The method of claim 11, wherein the inflammation is positively correlated with an age-related disease.

13. The pharmaceutical composition of claim 1, wherein the compound is selected from the following:
2-acetyl-5-[4-(N,N-dimethylamino)phenyl]-1,3-cyclohexanedione, 2-cyclopentanecarbonyl-5-[4-methylphenyl]-1,3-cyclohexanedione, 2-cyclopentanecarbonyl-5-[4-(1-methylethyl)phenyl]-1,3-cyclohexanedione, 2-cyclopentanecarbonyl-5-[4-chlorophenyl]-1,3-cyclohexanedione, 2-cyclopentanecarbonyl-5-[fur-2-yl]-1,3-cyclohexanedione, 2-isobutyryl-5-[fur-2-yl]-1,3-cyclohexanedione, 2-benzoyl-5-[2-chloro-6-fluorophenyl]-1,3-cyclohexanedione, 2-propanoyl-5-[4-methoxyphenyl]-1,3-cyclohexanedione, 2-acetyl-5-[3,4-dimethoxyphenyl]-1,3-cyclohexanedione, 2-benzoyl-5-[3,4-dimethoxyphenyl]-1,3-cyclohexanedione, 2-acetyl-5-[naphth-2-yl]-1,3-cyclohexanedione, 2-benzoyl-5-[2,4-dichlorophenyl]-1,3-cyclohexanedione, 2-propanoyl-5-[2,4,5-trimethoxyphenyl]-1,3-cyclohexanedione, 2-benzoyl-5-[4-fluorophenyl]-1,3-cyclohexanedione, 2-benzoyl-5-[4-methoxyphenyl]-1,3-cyclohexanedione, 2-benzoyl-5-[fur-2-yl]-1,3-cyclohexanedione, 2-cyclopropanecarbonyl-5-[4-methoxyphenyl]-1,3-cyclohexanedione, 2-cyclopentanecarbonyl-5-[4-methoxyphenyl]-1,3-cyclohexanedione, 2-isobutyryl-5[4-methoxyphenyl]-1,3-cyclohexanedione, 2-cyclopentanecarbonyl-5-phenyl-1,3-cyclohexanedione, 2-cyclopropanecarbonyl-5-[4-(N,N-dimethylamino)phenyl]-1,3-cyclohexanedione, 2-cyclopentanecarbonyl-5-[4-(N,N-dimethylamino)phenyl]-1,3-cyclohexanedione, 2-isobutyryl-5-[4-(N,N-dimethylamino)phenyl]-1,3-cyclohexanedione, 2-cyclopropanecarbonyl-5-[2,4,6-trimethylphenyl]-1,3-cyclohexanedione, 2-isobutyryl-5-[2,4,6-trimethylphenyl]-1,3-cyclohexanedione, 2-cyclopropanecarbonyl-5-[3,4-dimethoxyphenyl]-1,3-cyclonexanedione, 2-cyclopentanecarbonyl-5-[3,4-dimethoxyphenyl]-1,3-cyclohexanedione, 2-isobutyryl-5-[3,4-dimethoxyphenyl]-N,5-diphenyl-cyclohexane-1,3-dione-2-carboxarnide, N-phenyl-5-[4-fluorophenyl-cyclohexane-1,3-dione-2-carboxamide, N-phenyl-5-[2,4-dichlorophenyl-cyclohexane-1,3-dione-2-carboxamide; N-phenyl-5-[fur-2-yl]-cyclohexane-1,3-dione-2-carboxamide, N-phenyl-5-[2,4,6-trimethylphenyl]-cyclohexane-1,3-dione-2-carboxamide; N-phenyl-5-[3,4-dimethoxyphenyl]-cyclohexane-1,3-dione-2-carboxamide-1,3-cyclohexanedione, 2-cyclopropanecarbonyl-5-[4-(cyclopropanecarboxy)phenyl]-1,3-cyclohexanedione, 2-propanoyl-5-methyl-1,3-cyclohexanedione, 2-acetyl-5-methyl-1,3-cyclohexanedione, 2-propanoyl-5-[indol-3-yl]-1,3-cyclohexanedione, 2-propanoyl-5-ethyl-1,3-cyclohexanedione, 2-butyryl-5-[4-hydroxyphenyl]-1,3-cyclohexanedione, 2-propanoyl-5-cyclohexyl-1,3-cyclohexanedione, 2-propanoyl-5-[2-chloro-6-fluorophenyl]-1,3-cyclohexanedione, 2-propanoyl-5-[4-fluorophenyl]-1,3-cyclohexanedione, 2-propanoyl-5-[fur-2-yl]-1,3-cyclohexanedione, 2-cyclopropanecarbonyl-5-[2,4,6-trimethoxyphenyl]-1,3-cyclohexanedione, 2-cyclopentanecarbonyl-5-[2,4,6-trimethoxyphenyl]-1,3-cyclohexanedione, 2-isobutyryl-5-[2,4,6-trimethoxyphenyl]-1,3-cyclohexanedione, 2-cyclopropanecarbonyl-5-[4- methylphenyl]-1,3-cyclohexanedione, 2-isobutyryl-5-[4-methylphenyl]-1,3-cyclohexanedione, 2-isobutyryl-5-[4-(1-methylethyl)phenyl]-1,3-cyclohexanedione, 2-cyclopropanecarbonyl-5-[4-chlorophenyl]-1,3-cyclohexanedione, 2-isobutyryl-5-[4-chlorophenyl]-1,3-cyclohexanedione, 2-cyclopropanecarbonyl-5-[fur-2-yl]-1,3-cyclohexanedione, 2-cyclopropanecarbonyl-5-[4-fluorophenyl]-1,3-cyclohexanedione, 2-cyclopentanecarbonyl-5-[4-fluorophenyl]-1,3-cyclohexanedione, 2-isobutyryl-5-[4-fluorophenyl]-1,3-cyclohexanedione, 2-propanoyl-5-[2,4-dichlorophenyl]-1,3-cyclohexanedione, 2-acetyl-5-[2,4-dichlorophenyl]-1,3-cyclohexanedione, 2-butyryl-5-[fur-2-yl]-1,3-cyclohexanedione, 2-benzoyl-5-cyclohexyl-1,3-cyclohexanedione, 2-acetyl-5-[2-chloro-6-fluorophenyl]-1,3-cyclohexanedione, 2-acetyl-5-[fur-2-yl]-1,3-cyclohexanedione, 2-acetyl-5 [4-fluorophenyl]-1,3-cyclohexanedione, 2-propanoyl-5-[4(N,N-dimethylamino)phenyl]-1,3-cyclohexanedione, 2-acetyl-5-[bicyclo[2.2.1]hept-2-en-5-yl]-1,3-cyclohexanedione, 2-propanoyl-5-[(3,4-ethylenedioxy)phenyl]-1,3-cyclohexanedione, 2-cyclopropanecarbonyl-5-phenyl-1,3-cyclohexanedione, 2-isobutyryl-5-phenyl-1,3-cyclohexanedione, 2-cyclopropanecarbonyl-5-[2,4-dichlorophenyl]-1,3-cyclohexanedione, 2-isobutyryl-5-[2,4-dichlorophenyl]-1,3-cyclohexanedione, 2-cyclopropanecarbonyl-5-[thien-2-yl]-1,3-cyclohexanedione, 2-isobutyryl-5-[thien-2-yl]-1,3-cyclohexanedione, 2-acetyl-5-hexyl-1,3-cyclohexanedione, 2-propanoyl-5-hexyl-1,3-cyclohexanedione, 2-propanoyl-5-[thien-2-yl]-1,3-cyclohexanedione, 2-acetyl-5-(1-methylethyl)-1,3-cyclohexanedione, 2-propanoyl-5-(1-methylethyl)-1,3-cyclohexanedione, 2-acetyl-5-[thien-2-yl]-1,3-cyclohexanedione, 2-acetyl-5-[4-hydroxyphenyl]-1,3-cyclohexanedione, 2-acetyl-5-[3,4-methylepedioxyphenyl]-1,3-cyclohexanedione, 2-propanoyl-5-[3,4-methylenedioxyphenyl]-1,3-cyclohexanedione, 2-acetyl-5-[3,4-ethylenedioxyphenyl]-1,3-cyclohexanedione, 2-acetyl-5-[N-methylindol-3-yl]-1,3-cyclohexanedione, 2-acetyl-5-ethyl-1,3-cyclohexanedione, 2-acetyl-5-butyl-1,3-cyclohexanedione, 2-propanoyl-5-butyl-1,3-cyclohexanedione, 2-acetyl-5-pentyl-1,3-cyclohexanedione, 2-propanoyl-5-pentyl-1,3-cyclohexanedione, 2-butyryl-5-[N-methylindol-3-yl]-1,3-cyclohexanedione, and 2-propanoyl-5-[bicyclo[2.2.1]hept-2-en-5-yl]-1,3-cyclohexanedione.

\* \* \* \* \*